(12) United States Patent
Oritani et al.

(10) Patent No.: US 6,518,043 B1
(45) Date of Patent: Feb. 11, 2003

(54) PROTEINS SUPPRESSING PROLIFERATION OF LYMPHO-HEMATOPOIETIC CELLS

(75) Inventors: Kenji Oritani, Osaka (JP); Yoshiaki Tomiyama, Hyogo (JP); Yuji Matsuzawa, Hyogo (JP); Paul W. Kincade, Oklahoma City, OK (US)

(73) Assignees: Oklahoma Medical Research Foundation, Oklahoma, OK (US); Center for Advanced Science and Technology Incubation, Ltd., Chiyoda (JP)

( * ) Notice: Subject to any disclaimer, the term of this patent is extended or adjusted under 35 U.S.C. 154(b) by 0 days.

(21) Appl. No.: 09/523,686

(22) Filed: Mar. 13, 2000

(30) Foreign Application Priority Data

Apr. 14, 1999 (JP) .......................................... 11-107246

(51) Int. Cl.[7] .......................... C12P 21/06; C07K 1/00; C07K 14/00; C07K 17/00
(52) U.S. Cl. ...................................... 435/69.1; 530/350
(58) Field of Search .......................... 530/350; 435/69.1

(56) References Cited

U.S. PATENT DOCUMENTS 5,310,729 A * 5/1994 Lernhardt

OTHER PUBLICATIONS

Burgess et al., J of Cell Bio. 111:2129–2138, 1990.*

Lazar et al. Molecular and Cellular Biology 8:1247–1252, 1988.*

Bowie et al. Science, 247:1306–1310, 1990.*

Kincade et al., *Adv. Exp. Med. Biol.*, 292:227–234 (1991).

Oritani et al., Abstract of Workshop for Hematopoeitic Stem Cells, Presentation No. 9, the 61st Annual Meeting of the Japanese Society of Hematology (Apr. 19–21, 2000).

* cited by examiner

*Primary Examiner*—Anthony C. Caputa
*Assistant Examiner*—Natalie Davis
(74) *Attorney, Agent, or Firm*—Karl Boziecevic; James S. Keddie; Boziecevic, Field & Francis LLP

(57) ABSTRACT

A novel protein having the activity to suppress proliferation of lympho-hematopoietic cells derived from BNS2.4 cells, its gene, a method for preparing them and their uses are provided. The novel protein has been identified from a stromal cell line BMS2.4 by expression cloning targeting mouse myelomonocytic leukemia cell line WEHI3. This protein and its gene are useful for treating lympho-hematopoietic disorders.

9 Claims, 10 Drawing Sheets

Figure 2

```
  1 AGAAGTCGCGTCCAGCGTCCAGCGCAGCGCAGGCAGTCAGCGAGCAAGAGCCCGAAGCTC  60

61 CGAGTGAACTATTAAAGCAGCAAACTCCAGGCTCA ATG GGAAGGCGGCCTTGCCCTCGCG 120
                                       M  G  R  R  P  C  P  R  A

121 CTCCCCCTGCAGGCCAGCCCCGCAATCGTCAAGCTTCAG ATG CTGCCTGTGCATCTATT 180
     P  P  A  G  Q  P  R  N  R  Q  A  S  A  C  L  C  I  Y  S
                                             M  L  P  V  H  L  F

181 CCTGGTGGGAGGGGTGATGCTGAGCTGCAGCCCAGCCAGCTCACTTGATTCTGGTAAATC 240
     W  W  E  G  *
     L  V  G  G  V  M  L  S  C  S  P  A  S  S  L  D  S  G  K  S

241 TGGGAGCCTGCACCTGGAGCGCAGCGAAACCGCGCGCTTCCTAGCAGAGCTCCGAAGCGT 300
     G  S  L  H  L  E  R  S  E  T  A  R  F  L  A  E  L  R  S  V

301 GCCGGGTCACCAGTGCCTGCGGGACAGGACCGATTTCCCATGTCCCTGGAAGGAAGGAAC 360
     P  G  H  Q  C  L  R  D  R  T  D  F  P  C  P  W  K  E  G  T

361 TAACATCACACAGATGACTCTGGGAGAAACCACCAGTTGCTACTCCCAGACCCTCAGGCA 420
      N  I  T  Q  M  T  L  G  E  T  T  S  C  Y  S  Q  T  L  R  Q

421 GGTCCTCCACCTCTTTGACACAGAGGCCAGCAGAGCTGCCTGGCACGAGAGGGCGCTGGA 480
     V  L  H  L  F  D  T  E  A  S  R  A  A  W  H  E  R  A  L  D

481 CCAGCTACTATCTAGCCTGTGGCGTGAGCTGCAAGTGCTGAAGAGCCCAAGAGAGCAGGG 540
     Q  L  L  S  S  L  W  R  E  L  Q  V  L  K  S  P  R  E  Q  G

541 CCAGTCCTGTCCACTGCCTTTTGCCCTGGCCATCCGCACCTACTTCCGAGGGTTCTTCCG 600
     Q  S  C  P  L  P  F  A  L  A  I  R  T  Y  F  R  G  F  F  R

601 CTATCTGAAGGCAAAGGCACACAGCGCTTGCTCCTGGGAGATCGTCAGAGTCCAATTGCA 660
     Y  L  K  A  K  A  H  S  A  C  S  W  E  I  V  R  V  Q  L  Q

661 AGTGGACCTTCCAGCGTTCCCACTGTCTGCGAGAAGAGGCCCAAGATGAGGAGAAGCCCC 720
     V  D  L  P  A  F  P  L  S  A  R  R  G  P  R  *

721 GTGCAGGAATCTCTCTGCTCTCGTGACACCACGCTCCCTCTCTCCATTCAAAGCAGACGC 780

781 ACGGATTCGGATTCAGCACCAACAGGCGAAATGGGCATGCATCGACCAAGAACATCGAGT 840

841 TCTTTATGTCTTCCCTGCCAGAGGCCCCGAAGCATCCTACTGTACATCATACACTGCGAA 900

901 AGATGTTTGAAAGAAAACCTGTGCTCTTGCATTTGAGGTGGCTTCTGAATAAATTGATGA 960

961 TCTCGGTTAAAAAAAAAAAAAAAAAAAAAAAAAAAAA 997
```

Figure 4

```
           1        10        20        30        40        50        60
BGIF       MLPVHLFLVGGVMLSCSPASSLDSGKSGSLHL-ERSETARFLAELRSVPGHQCLRDRTDFP
IFN-α2     *ARLCA***MLIVM*YWSIC**GCDLPHTYN*-RNKRALKV**QM*RL*FLSKQ**G
IFN-β        MNNRWILHAAF*L*FSTTA*-*INYKQ*Q*Q**TNIRKCQEL*EQLN*KIN*TY*A**K 70        80        90       100       110       120
BGIF       CPWKEGTNITQMTLGETTSCYSQTLRQVLHLFDTEASRAAWHERALDQLLSSLWRELQVL
IFN-α2     F*LEKVD*-Q*IQKAQAIPVLRDLTQ*T*NTSKS*NATLSFCND*HQQ*ND*
IFN-β      I*M-*M*E--K*QKSY*AFAIQEM*QN*FLV*RNNF*STG*N*TIVVR**DE*HQQTVF*

130            140       150       160       170
BGIF       KSPREQG---QSCPLP-----FALAIRTYFRGFFRYLKAKAHSACSWEIVRVQLQVDLPAFP
IFN-α2     QTCLM*QVGV*EP**TQED--AL**V*K**HRITV**RE*K**PCA**V**AEVWRALSSSV
IFN-β      *TVL*EK---*EER*TWEMSST**HLKS*YWRVQ****LMKYNSYA*MV**AEIFRNFLIIR

180
BGIF       LSARRGPR
IFN-α2     NLLP*LSEEKE
IFN-β      RLTRNFQN
```

Figure 9
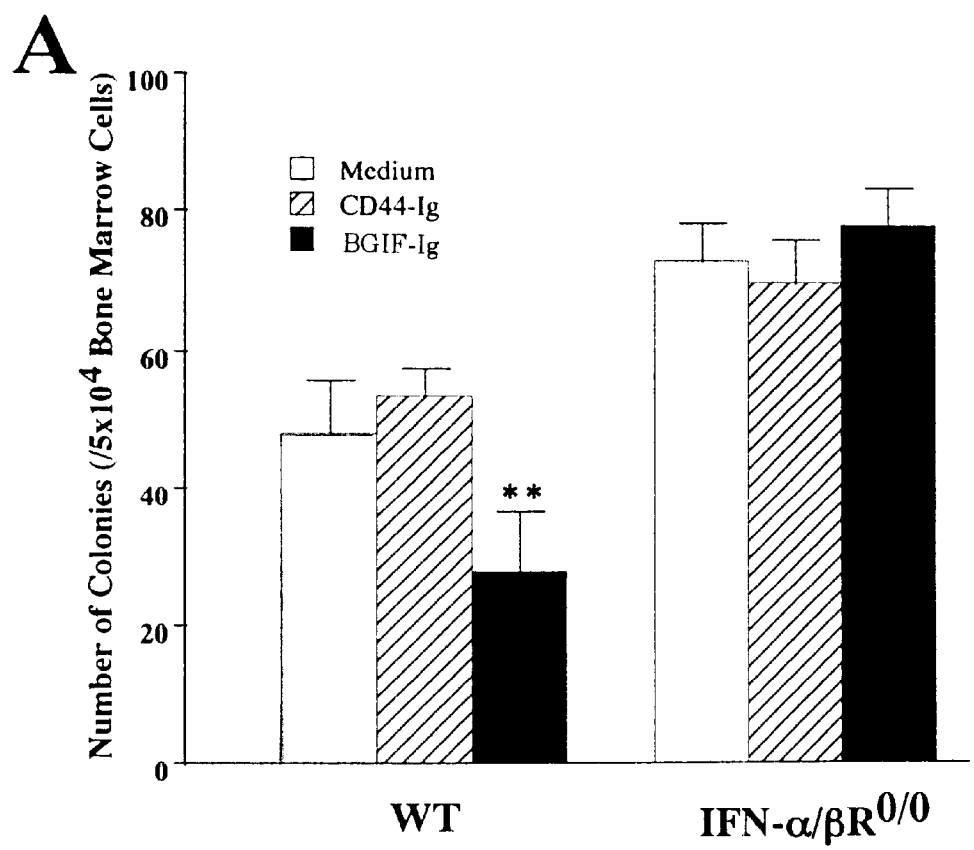
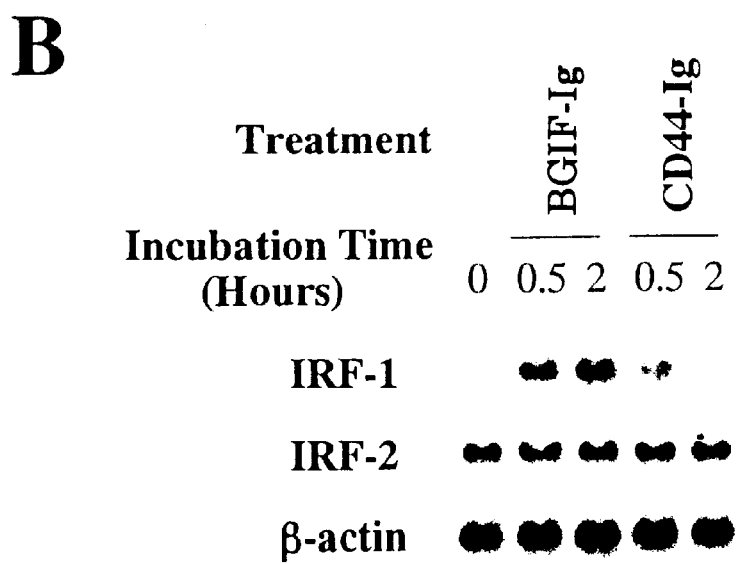

US 6,518,043 B1

PROTEINS SUPPRESSING PROLIFERATION OF LYMPHO-HEMATOPOIETIC CELLS

This application claims benefit of foreign priority from Japan application 11/107246, filed Apr. 14, 1999.

FIELD OF THE INVENTION

The present invention relates to a novel polypeptide derived from BMS2.4 cells, a gene thereof, a method for preparing the polypeptide and the gene, and uses thereof.

BACKGROUND OF THE INVENTION

Production of blood cells is strictly regulated by various stromal elements including adhesion molecules, extracellular matrix, and cytokines. Complex interactions between stromal and hematopoietic cells are essential for the movement of hematopoietic stem/progenitor cells within or from bone marrow, for the control of production of blood cells, and for the elimination of defective and harmful cells.

Long-term bone marrow cultures are in vitro system that mirror some in vivo relationships and provide an approach to define molecular and cellular interactions that may regulate production of blood cells. Pre-B cells could be displaced from the adherent layer of long-term bone marrow cultures by addition of antibodies to very late antigen-4 (VLA-4) or vascular cell adhesion molecule-1, and these reagents completely blocked lymphopoiesis in Whitlock-Witte (W/W) cultures. Antibodies to CD44 completely blocked production of lymphoid and myeloid cells in long-term bone marrow cultures. Addition of an antibody to CD9 cause strong adhesion between myeloid and stromal cells, and blocked the production of myeloid cells in Dexter cultures. These molecules might participate in cell-cell interactions critical for adhesion and movement of maturing hematopoietic cells in bone marrow.

Extracellular matrix delivers signals for survival and/or expansion of lympho-hematopoietic cells as well as immobilizes growth factors. Binding of fibronectin to integrins augments responsiveness of hematopoietic stem/progenitors to colony-stimulating factors. In contrast, interactions between fibronectin and VLA-5 cause apoptosis in a myeloid cell line. Hyaluronan, a ligand of CD44, forms viscous and hydrated gels and facilitates cell-cell adhesion and cell migration. Thrombospondin binds to hematopoietic progenitors, and hemonectin to myeloid precursors. Matrix glycoprotein SC1/ECM2 binds to B lineage cells and enhances their growth. Osteonectin not only acts as an anti-adhesive molecule but also immobilizes platelet derived growth factor.

Proliferation of primitive hematopoietic progenitors is regulated by interacting groups of cytokines. Interleukin-3 (IL-3), IL-4, and granulocyte/macrophage-colony-stimulating factor (GM-CSF) support proliferation of progenitors that exit from the dormant state. IL-6, IL-11, IL-12, granulocyte-CSF (G-CSF), and leukemia inhibitory factor (LIF) work synergistically with IL-3, IL-4, and GM-CSF to support proliferation of multipotential progenitors from cell-cycle dormant progenitors. Stem cell factor (SCF) and flt3-ligand not only support self-renewal of hematopoietic stem cells but also function as co-factors with other cytokines in promoting differentiation and expansion of hematopoietic progenitors. On the other hand, transforming growth factor-$\beta$ (TGF-$\beta$), tumor necrosis factor-$\alpha$ (TNF-$\alpha$), interferon-$\alpha/\beta$ (IFN-$\alpha/\beta$), and IFN-$\gamma$ are downregulators of lympho-hematopoiesis. Growth arrest and/or apoptosis of hematopoietic cells are induced by these factors. These regulatory cytokines are typically made in extremely small quantities in hematopoietic organs. Some of them are capable of attachment to extracellular matrix, and certain other cytokines are synthesized as transmembrane as well as soluble forms.

A number of genes that may be involved in lympho-hematopoiesis have been identified by experiments using cloned stromal cell lines that were originally selected for the ability to support proliferation and/or differentiation of a particular type of hematopoietic cells. A stromal cell line, BMS2, that was established from adherent cells of long-term bone marrow cultures has been known to have capacity to support growth of pre-B cells (Pietrangeli, C. E. et al., Eur. J. Immunol., 18: 863–872, 1988). However, BMS2.4 cells, a subclone of BMS2, revealed unique characteristics that they interfered with proliferation of hematopoietic cells (Kincade, P. W. et al., Adv. Exp. Med. Biol., 292: 227–234, 1991). However, its molecular mechanism is not known. An understanding of these molecules may be informative about negative regulator circuits that can potentially limit blood cell formation under steady state. These molecules may be helpful for understanding pathogenic mechanisms of lympho-hematopoietic disorders or treating such diseases.

SUMMARY OF THE INVENTION

An objective of this invention is to provide a novel protein derived from BMS2.4 cells that interferes with the proliferation of lympho-hematopoietic cells, a gene thereof, a method for preparing them, and uses thereof.

The present inventors transfected human renal carcinoma cell strain 293T with a cDNA library derived from a mouse stromal cell line, BMS2.4, and performed expression cloning based on growth inhibitory effects of the culture supernatant of transformants on myelomonocytic leukemia cell line, WEHI3. As a result, we succeeded in isolating a gene encoding a novel protein, designated Blood Cell Growth-Inhibiting Factor (BGIF) that interfered with proliferation of WEHI3 cells in a similar manner as the culture supernatant of BMS2.4 cells. A putative BGIF protein from the isolated gene is homologous to IFN-$\alpha$ and IFN-$\beta$, and expressed in stromal cells in bone marrow and spleen.

The present inventors prepared a recombinant BGIF protein to examine its effects on the growth of various lympho-hematopoietic cells. The recombinant BGIF protein suppressed proliferation of various (pre-)B lineage cell clones (1A9, BC7.12, BC7.7, F10, 2E8, 18-81, 7OZ/3, WEHI231, WEHI279, and SP2/0), T lineage lymphoma cell line, BW1597, and multipotent cell line EML-C1, as well as WEHI3 cells. BGIF arrests the cell cycle of WEHI3 cells at the G0/G1 phase and prolongs the G1 phase. It induces apoptosis in BC7.12 cells. It also suppressed the establishment of functional adherent layers in W/W culture.

Like type I IFNs, BGIF induced IFN regulatory factor-I utlizing IFN-$\alpha/\beta$ receptors, and activated JAK2 in myelomonocytic leukocyte line.

BGIF protein and its gene of this invention are associated with the lympho-hematopoietic system, and will be a useful tool for elucidating pathogenic mechanisms of lympho-hematopoietic disorders. BGIF protein of this invention would be applicable to therapeutics for various disorders in which the protein is involved.

Examples of disorders to be treated with the BGIF protein or its gene of this invention include lymphocytoma/hematapostemia such as acute lymphocytic or myelocytic leukemia, chronic lymphocytic or myelocytic leukemia, and malignant lymphoma, collagen diseases such as rheumatoid arthritis and systemic lupus erythematosus, idiopathic thrombocytopenic purpura, etc. The protein or the gene can also be used as immunoregulators. Disorders to be treated with compounds that inhibit the activity of BGIF protein include those accompanied by hematopenia such as aplastic anemia. These compounds can also be used as immunoregulators.

This invention relates to a novel protein derived from BMS2.4 cells that inhibits proliferation of lympho-hematopoietic cells, a gene thereof, and a method for preparing the protein and the gene, and uses thereof. More specifically, it relates to:

(1) a protein that suppresses the proliferation of lympho-hematopoietic cells selected from the group consisting of:

(a) a protein comprising the amino acid sequence as set forth in SEQ ID NO: 3;

(b) a protein comprising a derivative of the amino acid sequence set forth in SEQ ID NO: 3, in which one or more amino acids are substituted, deleted, inserted, and/or added; and (c) a protein encoded by a DNA hybridizing with the DNA comprising the nucleotide sequence as set forth in SEQ ID NO: 1, (2) the protein according to (1), wherein the lympho-hematopoietic cells are selected from the group consisting of B lineage cell line, 1A9, BC7.12, BC7.7, F10, 2E8, 18-81, 7OZ/3, WEHI231 and SP2/0, T lineage lymphoma cell line BW1597, and myelomonocytic leukemia cell line WEHI3, (3) a DNA encoding the protein according to (1), (4) the DNA of (3) comprising the coding region of the nucleotide sequence as set forth in SEQ ID NO: 1, (5) a vector comprising the DNA of (3), (6) a host cell retaining the vector of (5), (7) a method for preparing the protein of (1), the method comprising culturing the host cell of (6) and recovering recombinant proteins expressed in the cell from the cultured cell or culture supernatant thereof, (8) an antibody to the protein according to (1), (9) a peptide fragment of the protein according to (1),

(10) a DNA specifically hybridizing with the DNA comprising the nucleotide sequence as set forth in SEQ ID NO: 1 and comprises at least 15 nucleotides,

(11) a method for screening a compound binding to the protein according to (1), the method comprising (a) contacting the protein of (1) or its fragment with a test sample, (b) detecting the binding activity of the test sample to the protein or its fragment, and (c) selecting a compound that binds to the protein or its fragment,

(12) a compound that is isolable by the method according to (11) and binds to the protein of (1),

(13) a method for screening a compound that interferes with the activity of the protein according to (1) to suppress proliferation of lympho-hematopoietic cells, the method comprising (a) contacting the protein according to (1) with lympho-hematopoietic cells in the presence of a test sample, (b) detecting the proliferation of the cells, and (c) selecting a compound that interferes with the activity of the protein according to (1) to suppress proliferation of lympho-hematopoietic cells as compared with a control where the detection is performed in the absence of the test compound,

(14) the method according to (13), wherein said lympho-hematopoietic cells are selected from the group consisting of B lineage cell lines, 1A9, BC7.12, BC7.7, F10, 2E8, 18-81, 7OZ/3, WEHI231 and SP2/0, T lineage lymphoma cell line BW1597, and myelomonocytic leukemia cell line WEHI3,

(15) a compound isolable by the method according to (13), which interferes with the activity of the protein according to (1) to suppress proliferation of lympho-hematopoietic cells,

(16) a pharmaceutical composition comprising the protein according to (1) as an active ingredient,

(17) the pharmaceutical composition according to (16), wherein the composition is for treating lympho-hematopoietic disorders, and

(18) a pharmaceutical composition comprising the compound according to (12) as an active ingredient.

Herein, "lympho-hematopoietic cells" mean matured or precursor cells of erythrocytes, leukocytes or platelets.

BRIEF DESCRIPTION OF THE DRAWINGS

FIG. 2 shows nucleotide and deduced amino acid sequence of the 997 bp BGIF cDNA. The first and the second ATGs of BGIF are indicated square boxes. The deduced amino acid sequence translated from the first ATG is shown in an upper lane, and that translated from the second ATG is shown in a lower lane. The polyadenylation signal AATAAA is underlined.

FIG. 4 shows amino acid sequence alignment of BGIF, IFN-α and IFN-β. Asterisks indicate amino acid identities with BGIF. Dashed lines represent gaps introduced to align sequences.

Figure 6:
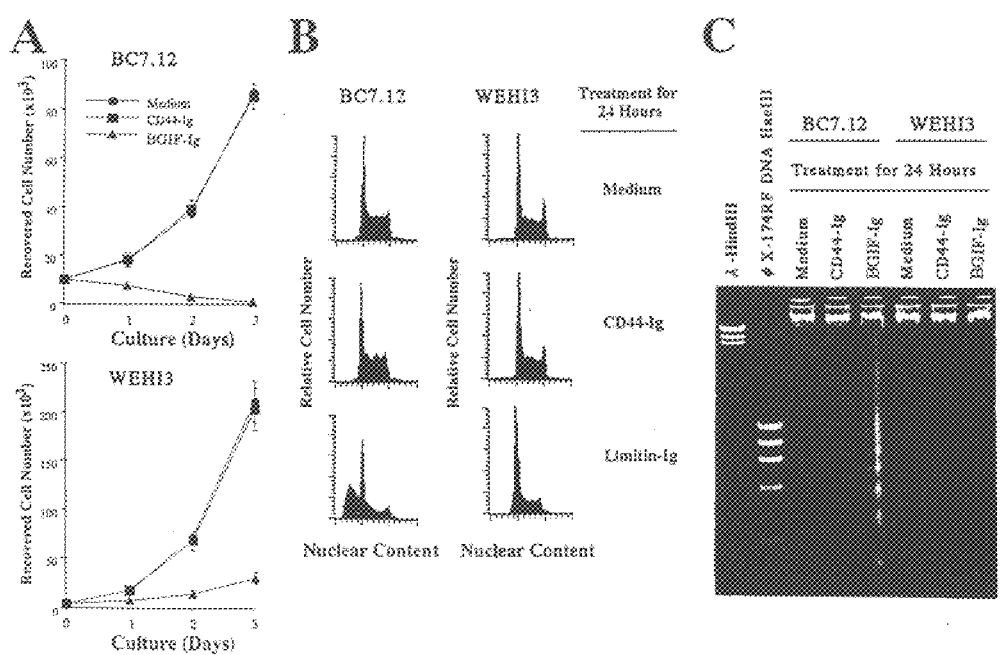

FIG. 6 illustrates that BGIF induces apoptosis in BC7.12 cells and G0/G1-arrest or G1-prolongation in WEHI3 cells. BC7.12 or WEHI3 cells were cultured with 100 ng/ml of CD44-Ig or BGIF-Ig for the indicated periods, and then subjected to cell viability (panel A), nuclear DNA content (panel B), and DNA fragmentation analysis (panel C). The results are representative of three similar experiments.

Figure 7:
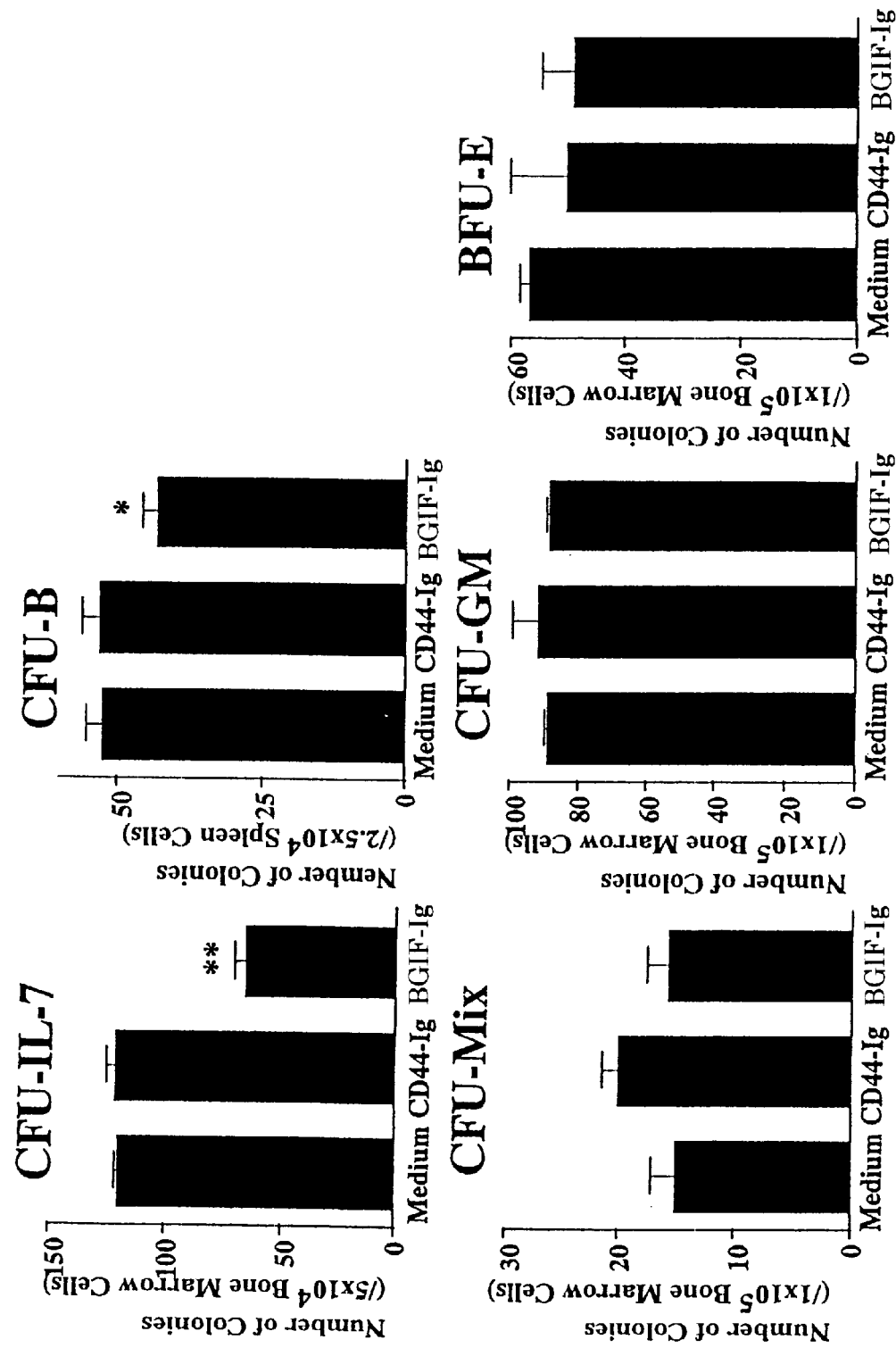

FIG. 7 illustrates that BGIF selectively inhibits the proliferation of normal lympho-hematopoietic progenitors. BGIF-Ig or CD44-Ig (100 ng/ml) was added to CFU-IL-7 and CFU-B (panel A) and CFU-mix, CFU-GM, and BFU-E (panel B) colony assays. The results are shown as means±SD of triplicate cultures. Statistically significant differences from control values are indicated by one ($p<0.05$) or two ($p<0.01$) asterisks. Similar results were obtained in five independent experiments.

Figure 8:
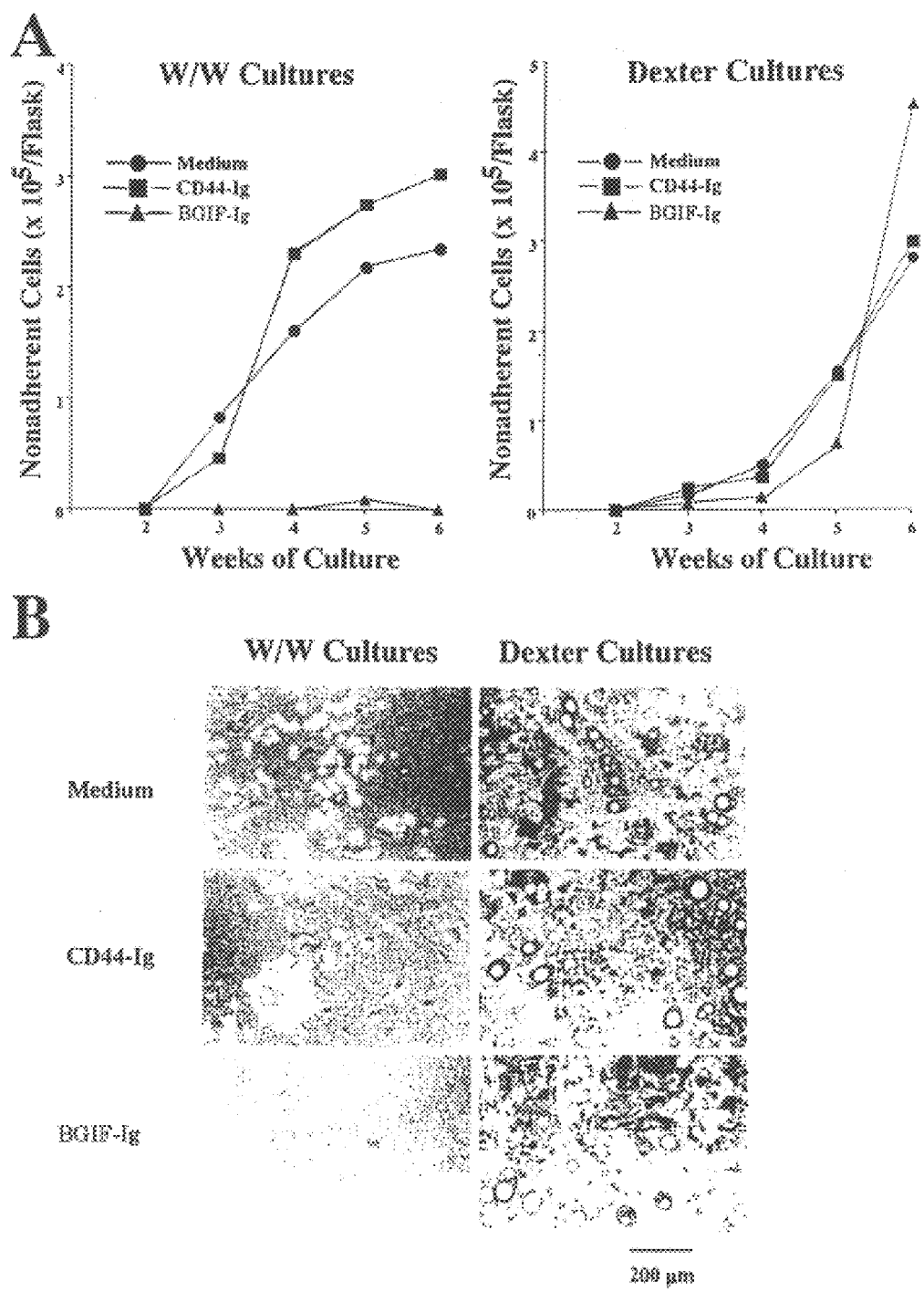

FIG. 8 shows effects of BGIF on LTBMC. Panel A presents that BGIF inhibits the production of B lymphocytes in W/W cultures. Replicate cultures of mouse bone marrow cells were prepared and maintained in the continuous presence of 100 ng/ml BGIF-Ig, CD44-Ig or medium alone. Numbers of non-adherent cells collected at weekly intervals were expressed as means per flask. Similar results were observed in three independent experiments. Panel B shows that BGIF inhibits the establishment of adherent layers in W/W cultures. Phase-contrast micrographs (photographed at 20× magnification) are shown of six weeks of W/W and Dexter cultures. Each figure shows one of three similar experiments.

FIG. 9 illustrates that BGIF utilizes the IFN-α/β receptors. Panel A shows that BGIF influences B lineage lymphocytes via the IFN-α/β receptors. Bone marrow cells ($5\times10^4$) were prepared from wild type (WT) or IFN-α/β receptor knock out mice (IFN-α/βR$^{0/0}$), and subjected to CFU-IL-7 colony assays in the presence of 100 ng/ml of BGIF-Ig or CD44-Ig. The results are shown as means ±SD of triplicate cultures. Statistically significant differences from control values are indicated by two ($p<0.01$) asterisks. Similar results were obtained in two independent experiments. Panel B shows the results of Northern blot analysis indicating IRF-1 induction by BGIF. WEHI3 cells ($1\times10^7$) were serum-starved for 1 h and then stimulated with 100 ng/ml CD44-Ig or BGIF-Ig for the indicated periods. Total cellular RNAs were isolated using TRIzol Reagent, and 15 μg of each sample was electrophoresed on formaldehyde agarose gels. The filters were hybridized with $^{32}$P-labeled probes for the indicated genes. Each figure shows one of three similar experiments.

Figure 10:
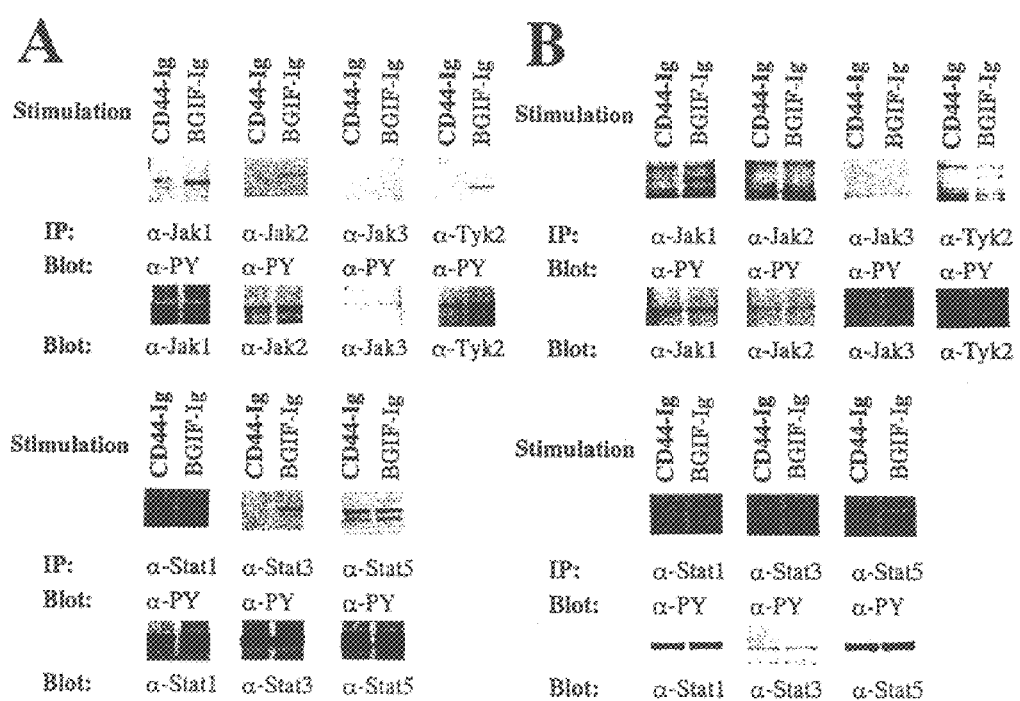

FIG. 10 shows signal transduction pathway utilized by BGIF. WEHI3 (panel A) and BC7.12 (panel B) cells ($1\times10^7$) were respectively serum-starved for 1 h and then stimulated with 100 ng/ml CD44-Ig or BGIF-Ig for 10 min. Total cell lysates were immunoprecipitated with the indicated antibodies and blots were probed with an anti-phosphotyrosine antibody. Filters were then stripped and reprobed with the indicated antibodies. Similar results were obtained in four independent experiments.

DETAILED DESCRIPTION OF THE INVENTION

This invention relates to a novel protein designated as BGIF, which is derived from BMS2.4 cells and inhibits proliferation of lympho-hematopoietic cells. The nucleotide sequence of the isolated BGIF cDNA, which is included in this invention, is shown in SEQ ID NO: 1, and amino acid sequence of BGIF protein encoded by said cDNA is represented in SEQ ID NO: 3.

The gene encoding BGIF protein was isolated by transfecting human renal carcinoma cell line 293T with a cDNA library derived from the mouse stromal cell line BMS2.4, and conducting the expression cloning of cDNA based on growth inhibitory effects of the culture supernatant of the transformed 293T cells on a myelomonocytic leukemia cell line WEHI3.

The mouse BGIF gene of this invention contains an open reading frame encoding a protein comprising 182 amino acid residues (FIG. 2). The protein has a highly hydrophobic stretch of 21 amino acid residues at the N-terminal end, but lacks an internal membrane spanning domain, suggesting that BGIF is a secreted protein. The amino acid sequence of the protein contains one Asn-X-Ser/Thr potential N-linked glycosylation sites at the position of amino acid 68, consistent with the hypothesis that BGIF may be glycosylated. As a result of computer search of BGIF sequence using FASTA and BLAST programs, BGIF has a similarity with IFN-α (31.9% identity in 166 amino acids overlap) and IFN-β (25.9% identity in 166 amino acids overlap) at the amino acid level (FIG. 4). However, six cystaine residues in the BGIF protein were not identical to those of IFN-α or IFN-β.

Figure 5:
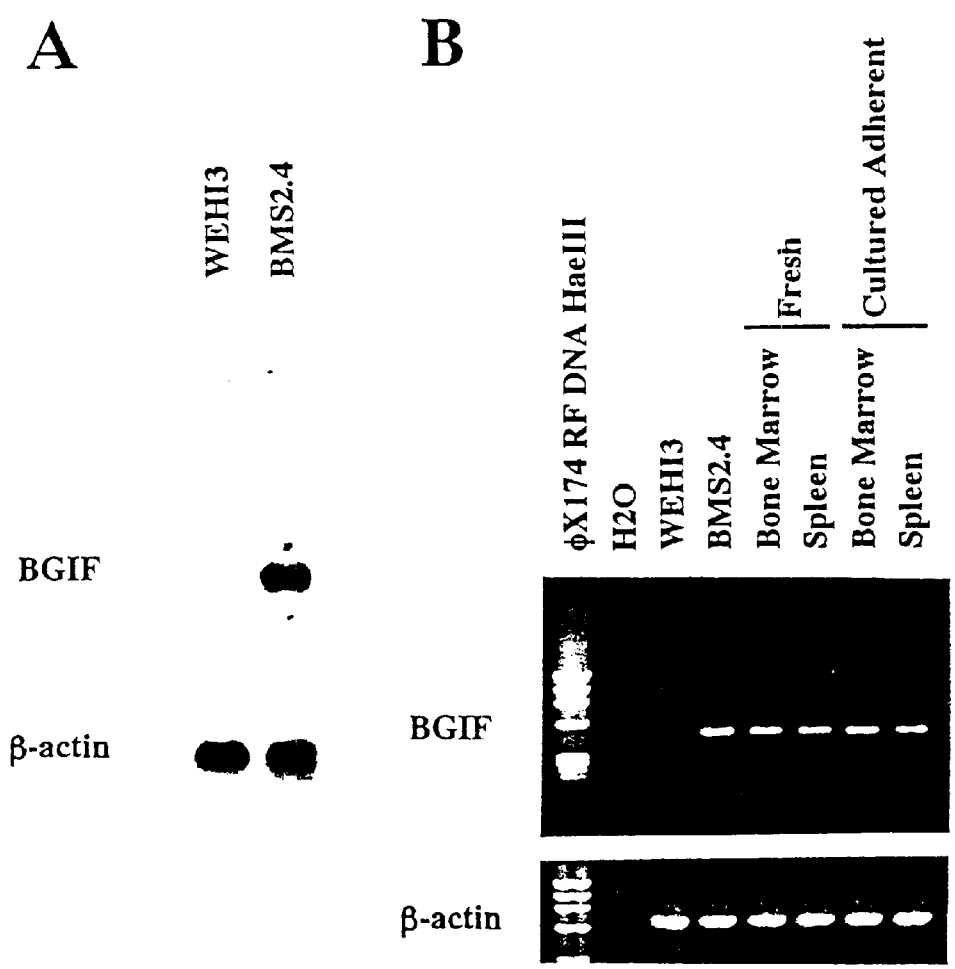
FIG. 5 shows expression of BGIF in lympho-hematopoietic organs. (A) presents results of Northern blot analysis of polyA+ RNAs (5 μg/lane) isolated from WEHI3 and BMS2.4 cells. The lower panel is a control for equal loading where the same blot was probed with β-actin. (B) presents electrophoretic patterns PCR products of total RNAs isolated from various cells. Total RNAs (2.5 μg) were isolated from the indicated cells, and subjected to RT-PCR. The amplified products were electrophoresed through a 1% agarose gel containing ethidium bromide.

Northern blot analysis revealed that the message size of BGIF was approximately 1 kb and that BMS2.4, but not WEHI3, expressed BGIF mRNA (FIG. 5A). In addition, RT-PCR was used to survey expression in mouse bone marrow, spleen adherent cells as well as freshly isolated bone marrow or spleen cells (FIG. 5B). Therefore, BGIF mRNA is expressed in bone marrow and spleen, at least by some of bone marrow and spleen stromal cells.

A BGIF fusion protein suppressed proliferation of B lineage cell lines (1A9, BC7.12, BC7.7, F10, 2E8, 18-81, 7OZ/3, WEHI231, SP2/0), a T lymphoma cell line (BW1597), and a myelomonocytic leukemia cell line (WEHI3 and WEHI279) and a mouse multipotent cell line (EML-C1). While most of the cell lines did not die, three of long-term bone marrow culture derived pre-B cell clones (1A9, BC7.12, 2E8) lost their viability by the treatment of the BGIF fusion protein. In contrast, lymphoma cell lines (BCL1 and EL4) and a myeloid cell line (M1) were not affected by the BGIF fusion protein (Table 1). Therefore, BGIF suppresses growth of a variety of lympho-hematopoietic cell lines.

Semisolid agar cloning assays were then used to evaluate the direct influence of BGIF on colony formation of lympho-hematopoietic progenitors. The cloning efficiency of IL-7 responding pre-B cells (CFU-IL-7) was decreased by addition of the BGIF fusion protein (FIG. 7). BGIF induced G0/G1-arrest or G1-prolongation in WEHI3 cells, and apoptosis in BC7.12 cells (FIG. 6). BGIF also suppressed the establishment of adherent layers in W/W cultures (FIG. 8). Therefore, BGIF suppresses proliferation of not only transformed but also normal lympho-hematopoietic cells.

BGIF, like type I IFN, also induced the IFN regulatory factor 1 using IFN-α/β receptors, while it activated JAK2 in myelomonocytic leukemia cell lines (FIG. 9).

These facts indicate that the BGIF protein is a novel humoral factor that suppresses proliferation of lympho-hematopoietic cells. BGIF would thus be helpful for understanding pathogenic mechanisms of lympho-hematopoietic disorders and can be used as a drug for patients with lympho-hematopoietic diseases such as leukemias and malignant lymphomas, and for those with collagen diseases.

Collagen diseases are disorders which damage various organs by producing an autoantibody that recognizes the body's own cells. In rheumatoid arthritis and some other diseases, the activation of polyclonal B lymphocytes is observed. Since BGIF suppresses B lineage lymphocytopoiesis, it can be one of drugs for collagen diseases by suppressing either the production of an autoantibody or the activation of B lineage lymphocytopoiesis. In addition, the deficiency in a negative regulatory factor for the lymphocytopoiesis might be a cause of collagen diseases, and the reduction of BGIF production may thus be a cause of collagen diseases.

Proteins structurally similar to the mouse BGIF protein are also included in this invention as long as they have an activity to suppress proliferation of lympho-hematopoietic cells. Such structurally analogous proteins also include variants of BGIF protein and BGIF proteins derived from other organisms.

One skilled in the art would readily prepare these proteins using, for example, standard mutagenesis methods. Known methods for altering amino acids in proteins include site-specific mutagenesis, for example, the method of preparing deletion-mutant (Kowalski, D.,et al., 1976, J. Biochem., 15, 4457; McCutchan, T. F., et al., 1984, Science, 225, 626–628), Kunkel's method (Kunkel, T. A., 1985, Proc. Natl. Acad. Sci. USA, 82: 488–492; Kunkel, T. A. et al., 1987, Methods Enzymol., 154: 367–382), Gapped-duplex method Kramer, W. and Fritz, H.-J. 1987, Methods Enzymol., 154: 350–367; Zoller, M. J. and Smith, M., 1983, Methods Enzymol., 100: 468–500; Hirose, S., 1991, Muramatsu, M. & Okayama, H., eds., Jikken Igaku, extra issue, Genetic Engineering Handbook, Yodosha, pp246–252), PCR method (Muramatsu, M., ed., Laboratory manual, Genetic Engineering, 3rd edition, Maruzen, 1996, pp227–230), cassette alteration method (Kishimoto, T., 1991, Muramatsu, M. & Okayama, H., ed., Jikken Igaku, extra issue, Genetic Engineering Handbook, Yodosha, pp253–260), etc. A Transformer™ Site-Directed Mutagenesis Kit (CLONTECH #K1600-1), for example, may be used.

In artificial alteration of amino acids in proteins, the number of amino acid residues to be altered is usually 30 or less, preferably 10 or less, and more preferably 5 or less. Alteration of amino acids in proteins could occur spontaneously. Such proteins having amino acid sequences different from that of the natural mouse BGIF protein (SEQ ID NO: 3) due to artificial or spontaneous substitution, deletion, addition and/or insertion of amino acid residues, are also included in this invention as long as they have an activity to suppress proliferation of lympho-hematopoietic cells.

An amino acid has similar properties to that of the amino acid to be substituted is preferably used for substitution. Since Ala, Val, Leu, Ile, Pro, Met, Phe and Trp are, for example, all classified into the non-polar amino acid, they are considered to have similar properties. Non-charged amino acids include Gly, Ser, Thr, Cys, Tyr, Asn, and Gln. Acidic amino acids include Asp and Glu, while basic amino acids include Lys, Arg and His.

The proteins formed by deleting some amino acid residues from the mouse BGIF according to this invention include proteins in which the signal sequence (SEQ ID NO: 4) is deleted. Proteins formed by adding amino acid residues to the mouse BGIF protein include a fusion protein of the mouse BGIF protein with other peptides.

Proteins structurally similar to the mouse BGIF protein having an activity to suppress proliferation of lympho-hematopoietic cells can be prepared using the known hybridization technique (Cell Engineering, extra issue, New Cell Engineering Experimental Protocol, 1991, Shujunsha, pp. 188–193, and Sambrook, J. et al., Molecular Cloning, Cold Spring Harbor Laboratory Press (1989), 8.46–8.52) and polymerase chain reaction (PCR) technique (Cell Engineering, extra issue, 8, New Cell Engineering Experimental Protocol, 1991, Shujunsha, pp. 171–186; Sambrook, J. et al., Molecular Cloning, Cold Spring Harbor Laboratory Press (1989), 14.1–14.35). It is routine for one skilled in the art to isolate DNA highly homologous to mouse BGIF cDNA from various other organisms using the mouse BGIF cDNA (SEQ ID NO: 1) or portions thereof as a probe and oligonucleotides specifically hybridizing with the mouse BGIF cDNA as a primer to obtain proteins structurally similar to the mouse BGIF protein from the isolated DNA.

Proteins encoded by DNAs hybridizing with the mouse BGIF cDNA are included in this invention as long as they suppress proliferation of lympho-hematopoietic cells. Other organisms used for isolating such proteins include, for example, humans, monkeys, rats, rabbits, goats, cattle, pigs, etc., but are not limited thereto. DNAs encoding such proteins can be isolated from such sources as bone marrow, spleen cells, lympho-hematopoietic cells, and cultured bone marrow/spleen stromal cells.

DNAs encoding the BGIF protein derived from animals other than mice are usually highly identical with the nucleotide sequence (SEQ ID NO: 1) of mouse BGIF cDNA. "Being highly identical" means at least 60% or more, preferably 80% or more, and further preferably 90% or more sequence identity at the amino acid level. Sequence homology can be determined by the homology search program of DNA Data Bank of Japan (National Institute of Genetics: Yata 1111, Mishima, Shizuoka 411, Japan).

One skilled in the art can readily determine conditions for hybridization to isolate DNAs encoding proteins functionally equivalent to the mouse BGIF protein. One example of hybridization conditions is as follows. After the pre-hybridization at 42 overnight in a hybridization solution containing 25% formamide (50% formamnide under the stringent conditions), 4×SSC, 50 mM Hepes pH 7.0, 10×Denhardt's solution and 20 μg/ml denatured salmon sperm DNA, a labeled probe is added, and the hybridization is performed by maintaining the reaction mixture at 42 overnight. Then, successive washings were performed at room temperature with 2×SSC and 0.1% SDS (at 50, 0.5× SSC and 0.1% SDS under the stringent conditions). In this case, although plural factors including the temperature, concentration of formamide, salt concentration, etc. are thought to influence the stringency of hybridization, one skilled in the art would readily determine the stringent conditions similar to above by suitably selecting these factors (Cell Technology, extra issue 8, New Cell Engineering Experimental Protocol Protocol.

The protein of this invention can be prepared as either natural proteins or recombinant proteins utilizing gene recombination techniques. Natural proteins can be prepared by subjecting tissue extracts that are supposed to contain the BGIF protein (for example, bone marrow and spleen cells) to affinity chromatography using the antibody to the BGIF protein as described below. On the other hand, recombinant proteins may be prepared by culturing cells transformed with DNA encoding the BGIF protein, allowing the transformants to express the protein, and recovering the protein.

The proteins of this invention also include partial peptides of the above-described proteins. Partial peptides of the proteins of this invention include, for example, those corresponding to the binding site of the protein to its receptor. Such partial peptides can be administered to the body to serve as agonists and antagonists of the receptors for the proteins of this invention, or as competitive inhibitors for the proteins. These partial peptides are useful as activators and inhibitors for the signal transduction mediated by the proteins of this invention. Partial peptides of this invention also include, for example, the N-terminal or C-terminal region of the protein of this invention in which the signal sequence is deleted, and said peptides can be used for the preparation of antibodies. Partial peptides comprising the amino acid sequence specific to the protein of this invention have at least 7, preferably at least 8, more preferably at least 9 amino acid residues. Partial peptides of this invention can be produced by genetic engineering techniques, known peptide synthetic methods, or by digestion of the protein of this invention with appropriate peptidases.

This invention also relates to DNAs encoding the proteins of the invention. DNAs encoding the protein of this invention are not particularly limited as long as they can encode the proteins of this invention, including cDNAs, genomic DNAs, and synthetic DNAs. DNAs having any desired nucleotide sequences based on the degeneracy of genetic codes are also included in this invention as long as they can encode the proteins of this invention.

cDNAs encoding the proteins of this invention can be screened, for example, by labeling cDNA of SEQ ID NO: 1 or segments thereof, RNAs complementary to them, or synthetic oligonucleotides comprising partial sequences of said cDNA with $^{32}$P, etc., and hybridizing them with a cDNA library derived from tissues (e.g., bone marrow, spleen, etc.) expressing the proteins of this invention. Such cDNAs can be cloned by synthesizing oligonucleotides corresponding to nucleotide sequences of these cDNAs, and amplifying them by PCR with cDNA derived from suitable tissues (e.g. bone marrow, spleen, etc.) as a template. The genomic DNA can be screened, for example, by labeling cDNA of SEQ ID NO: 1 or segments thereof, RNAs complementary to them, or synthetic oligonucleotides comprising partial sequences of said cDNA with $^{32}$P, etc., and hybridizing them with a genomic DNA library. Alternatively, cDNAs encoding the proteins of this invention can be cloned by synthesizing oligonucleotides corresponding to nucleotide sequences of these cDNAs, and amplifying them by PCR with a genomic DNA as a template. Synthetic DNAs can be prepared, for example, by chemically synthesizing oligonucleotides comprising partial sequences of cDNA of SEQ ID NO: 1, annealing them to form double strand, and ligating them with DNA ligase.

These DNAs are useful for the production of recombinant proteins. The proteins of this invention can be prepared as recombinant proteins by inserting DNAs encoding the proteins of this invention (e.g. DNA of SEQ ID NO: 1) into an appropriate expression vector, transforming suitable host cells with the vector, culturing the transformants, and purifying proteins expressed. When the proteins of this invention is a secretory protein, it can be prepared, for example, by expressing it in mammalian cells to be secreted therefrom.

Expression vectors to be specifically used in *E. coli* include, for example, pKK223-3, pKK233-2, pJLA502, etc. The proteins of this invention can be expressed, for example, as fused proteins with other proteins. Vectors for expressing such fusion proteins include, for example, pRIT2T, pGEX-2T, pGEX-3X, etc. These fused proteins can be easily collected using an affinity column. Only a desired protein can easily excised from the fusion protein when a vector is designed to provide the thrombin- or factor Xa-cleaving site between the desired protein and a partner protein in the fused protein. Vectors for secreting the proteins extracellularly or into the periplasm include pKT280, pRIT5, etc. (Okada, M. and Miyazaki, K. ed., Invincible Biotechnical Series, Protein Experimental Note, 1st volume, Extraction and Separation/Purification, Yodosha, 1996, pp.139–149).

It is also possible to express the proteins of this invention in insect and mammalian cells using baculoviruses. Baculovirus vectors used in mammalian cells are, for example, pAcCAGMCS1 (Muramatsu, M., ed., Labomanual Genetic Engineering, 3rd ed., Maruzen, 1996, pp. 242–246).

Recombinant proteins expressed in host cells can be purified by known methods. The protein of this invention expressed in the form of a fused protein, for example, with a histidine residue tag or glutathione-S-transferase (GST) attached at the N-terminus can be purified by a nickel column or a glutathione sepharose column, etc.

DNAs encoding the proteins of this invention can be applied to gene therapy for disorders caused by the mutation thereof. Vectors used for gene therapy include, for example, virus vectors such as retrovirus vector, adenovirus vector, adeno-associated virus vector, vaccinia virus vector, lentivirus vector, herpesvirus vector, alphavirus vector, EB virus vector, papilloma virus vector, foamy virus vector, etc., and non-viral vectors such as cationic liposomes, ligand-DNA complexes, gene guns, etc. (Y. Niitsu, M. Takahashi, Molecular Medicine, Vol. 35, No. 11, 1385–1395, 1998). Gene transfer can be carried out in vivo and ex vivo. The DNA encoding the protein of this invention can be co-transferred with other cytokine genes.

The present invention also relates to DNAs specifically hybridizing with the DNA comprising the nucleotide sequence of SEQ ID NO: 1 and containing at least 15 nucleotides. "Specifically hybridizing" means that DNA does not significantly cross-hybridize with DNAs encoding other proteins under usual hybridization conditions as described above, preferably under stringent hybridization conditions. Such DNAs include probes, primers, nucleotides or nucleotide derivatives (e.g. antisense oligonucleotides and lipozymes, etc.), which specifically hybridize with DNAs encoding the proteins of this invention, or DNAs complementary to said DNAs.

cDNAs encoding the proteins of this invention or oligonucleotides comprising partial sequences thereof can be used for cloning genes and cDNAs encoding the proteins of this invention, or amplifying them by PCR. The cDNAs and oligonucleotides can also be utilized for detecting polymorphism or abnormality (gene diagnosis, etc.) of the gene or cDNA by the restriction fragment length polymorphism (RFLP) method, single strand DNA conformation polymorphism (SSCP) method, etc.

This invention also relates to antibodies binding to the proteins of the invention. Antibodies of this invention include both polyclonal and monoclonal antibodies. Polyclonal antibodies can be prepared, for example, according to the method described in Institute of Medical Science, Section of Carcinostasis, University of Tokyo, ed., Cell Engineering, extra issue 8, New Cell Engineering Experimental Protocol, 1993, Shujunsha, pp. 202–217). The purified proteins of this invention, partial peptides thereof, or peptides synthesized based on amino acid sequences of the proteins of this invention are injected to animals to be immunized such as rabbits, guinea pigs, mice, chickens, etc. introperitoneally, subcutaneously, intramuscularly, or into the ear vein, groin, the back of appendicular nail, etc.

Antigenic proteins may be administered together with Freund's complete or incomplete adjuvants. Antigen is usually administered every several weeks. The titer can be elevated by the booster injection. Blood is periodically collected to confirm the titer elevation by ELISA, etc. After the final immunization, the blood is collected from immunized animals to obtain antisera. Antisera are purified by salting out, ion exchange chromatography, HPLC, etc. to obtain an IgG fraction. The antibody can be further purified by affinity chromatography using the immobilized antigen.

A monoclonal antibody can be prepared, for example, according to the method described in Koike, T. & Taniguchi, M. 1991, Jikken Igaku, extra issue, Genetic Engineering Handbook, Muramatsu, M. & Okayama, H., eds., Yodosha, pp 70–74). Animals are immunized with the protein of this invention or partial peptides thereof in a similar manner as described above, and, after the final immunization, spleen or lymph node is excised from immunized animals. Antibody-producing cells contained in the spleen or lymph node are fused with myeloma cells using a fusing agent such as polyethylene glycol, to prepare hybridomas. Desired hybridomas are screened and cultured to prepare a monoclonal antibody from the culture supernatant. The monoclonal antibody is purified by salting out, ion exchange chromatography, HPLC, etc. to obtain an IgG fraction. The resulting fraction can be further purified by affinity chromatography using the immobilized antigen.

Antibodies thus prepared are used for the affinity purification of the proteins of this invention. They can also be used for the test and diagnosis of disorders caused by abnormal expression and structural abnormality of the proteins of this invention and for detection of the expression level of the protein. Abnormality in expression and structure of the proteins of this invention can be examined and diagnosed by extracting proteins from, for example, tissues, blood or cells, and detecting the proteins of this invention using Western blotting, immunoprecipitation, ELISA, etc. Antibodies of this invention can be applied to the antibody treatment. For antibody treatment, they are preferably humanized or human antibodies.

Humanized monoclonal antibodies can be prepared according to, for example, a method described in H. Isogai, 1988, Jikken Igaku, Vol. 6, No. 10, 55–60. A method using molecular biological techniques as described in T. Tsunenari et al., 1996, Anticancer Res., 16, 2537–2544 can also be used. Human antibodies can be prepared by immunizing mice, in which the immune system is replaced by the human system, with the protein of this invention.

The present invention also relates to a method for screening a compound binding to the protein of this invention. The screening method of this invention comprises: (a) contacting the protein of this invention or partial peptides thereof with a test sample, (b) detecting the binding activity of the test sample to the protein of this invention or partial peptides thereof, and (c) selecting a compound that binds to the protein of this invention or partial peptides thereof.

Proteins binding to the protein of this invention can be screened, for example, by applying culture supernatants or extracts of cells, which are expectedly express proteins binding to the protein of this invention, to an affinity column to which the protein of this invention is attached (immobilized), and purifying proteins specifically binding to the column.

Alternatively, proteins binding to the protein of this invention can be screened by the West Western blotting method or two hybrid system. In the former method, a cDNA library using a phage vector is prepared from tissues or cells (for example, lympho-hematopoietic cells, etc.) which expectedly express proteins binding to the protein of this invention, and proteins are expressed from cloned cDNA on agarose, transferred to filter, fixed, and reacted with the labeled protein of this invention to detect plaques expressing binding proteins. In the latter method, the protein of this invention is expressed as a fusion protein with a test protein such as GAL4 DNA-binding region and GAL4 transcription activating region, and the binding of the protein of this invention to the test protein is detected by the expression of a reporter gene linked to the downstream from a promoter having the binding sequence of the GAL4 DNA-binding protein.

Other screening methods include the method comprising contacting synthetic compounds, natural proteins or random phage peptide display library with the immobilized protein of this invention and detecting binding molecules and the method comprising isolating compounds binding to the protein of this invention using a high-through put based on combinatorial chemical technique.

Test samples used for screening include, for example, cell extracts, expression products of a gene library, synthetic low molecular weight compounds, synthetic peptides, natural compounds, etc., but are not limited thereto. Those test samples used for screening may be labeled prior to use as the occasion demands. Labels include, for example, radioactive and fluorescent ones, etc., but are not limited to them.

This invention also relates to a method for screening receptors of the protein of the invention. The results obtained in examples below showed that many lympho-hematopoietic cells have responsiveness to the protein of this invention, suggesting that these cells are assumed to express receptors of the protein of this invention. Such receptors would thus be isolated using the proteins of this invention.

For example, receptors of the protein of this invention can be obtained by collecting proteins from cells which expectedly express a receptor of the protein of this invention, and subjecting the proteins to the above-described affinity chromatography. A DNA encoding the receptor can be isolated by raising an antibody to the receptor of the protein of this invention and screening a cDNA expression library prepared from cells which expectedly express the receptor of the protein of this invention using the antibody.

Alternatively, a DNA encoding the receptor of the protein of this invention can be screened by the subtractive hybridization method comprising preparing cDNAs from mRNA of cells responsive to the protein of this invention, hybridizing the cDNAs with mRNA of other cells unresponsive to the protein of this invention, and subtracting cDNAs hybridizing with mRNAs from both responsive and unresponsive cells to screen desired cDNAs. A DNA encoding the receptor of the protein of this invention can also be isolated by preparing cDNAs from cells which expectedly express the receptor of the protein of this invention, transforming cells with the cDNAs, and screening expressed proteins using the protein of this invention as a ligand, or the antibody to the receptor of the protein of this invention. It is also possible to prepare cDNAs from cells which expectedly express the receptor of the protein of this invention, to transform COS cells with the cDNAs to screen a DNA by monitoring the transient expression. Another method comprises preparing mRNA from cells which expectedly express the receptor of the protein of this invention, injecting the mRNA into oocytes of Xenopus laevis, and functionally screening the receptor. The DNA can also be cloned by hybridization and PCR based on homology to the known receptors of cytokines that are homologous to the protein of this invention (T. Yokota & K. Arai, eds., Jikken Igaku, extra issue, Biomanual seeries 3, Gene Cloning Method, 1993, pp. 99–156.

The invention also relates to a method for screening a compound that interferes with the activity of the protein of this invention to suppress proliferation of lympho-hematopoietic cells. This method uses the activity of the protein of this invention to suppress proliferation of lympho-hematopoietic cells as an indicator, and comprises the steps of (a) contacting a protein of this invention with lympho-hematopoietic cells in the presence of a test sample, (b) detecting proliferation of said cells, and (c) selecting a compound that interferes with the activity of the protein of this invention to suppress proliferation of said cells as compared with the activity detected in the absence of the test sample (control).

Test samples used for this screening method include, for example, cell extracts, expression products of a gene library, synthetic low molecular weight compounds, proteins, natural or synthetic peptides, natural products, sera, etc., but are not limited to them. The test samples can be compounds isolated by the above-described screening method monitoring the binding activity of the compounds to the protein of this invention. Proteins of this invention used for the screening method may be purified ones or culture supernatants of transformants secreting the proteins of this invention.

Any lympho-hematopoietic cells can be used for the screening method, without limitation, as long as their proliferations are suppressed by the proteins of this invention, Preferable cells include, for example, pre-B lineage cell lines, 1A9, BC7.12, BC7.7, F10, 2E8, 18-81, 7OZ/3, WEHI231 and SP2/0, T lineage lymphoma cell line BW1597, and myelomonocytic leukemia cell line WEHI3.

Growth of these cells is inhibited in the absence of a test compound since the proteins of this invention suppress proliferation of lympho-hematopoietic cells. When proliferation of the cells is suppressed in the presence of a test compound, the compound is judged as the compound that interfere with the activity of the proteins of this invention to suppress proliferation of lympho-hematopoietic cells. Herein, "interfering with the activity to suppress proliferation" includes "completely inhibiting the suppression of proliferation."

Compounds to be isolated by this screening method include, for example, 1) compounds binding to the protein of this invention to inhibit its activity, 2) compounds binding to the proteins of this invention or receptors thereof to inhibit the binding between the proteins of this invention and receptors thereof, 3) compounds binding to the receptors of proteins of this invention to inhibit activation of the receptors, and 4) compounds inhibiting signal transduction to express the phenotype of cell proliferation from the receptors of the proteins of this invention. These compounds can be used as drugs for preventing or treating disorders caused by abnormality of the signal transduction system mediated by the proteins of this invention (for example, diseases caused by abnormality of lympho-hematopoietic system).

When the proteins of this invention or compounds isolated by the screening methods of this invention are used as drugs, they may be administered to patients as they are or as pharmaceutical preparations produced by known methods. They can be formulated together with, for example, pharmaceutically acceptable carriers or media such as sterilized water, physiological saline, vegetable oil, emulsifiers, suspending agents, surfactants, stabilizers, etc. They may be administered to patients by methods well known in the art, for example, by intra-arterial, intravenous, subcutaneous injection. They can also be administered intranasally, intrabronchially, intramuscularly, or orally. Doses may vary depending on the body weight and age of patients as well as administration method, and can be suitably selected by those skilled in the art. When a DNA encoding the compound is known, gene therapy may be performed by inserting the DNA into a vector for gene therapy. Doses of DNA and method for its administration may vary depending on the body weight, age and symptoms of patients, but can be suitably selected by those skilled in the art.

BGIF proteins of this invention suppress proliferation of lympho-hematopoietic cells, and can thus be applied to diagnosis and treatment of lympho-hematopoietic disorders. BGIF proteins are also useful as a tool for elucidating pathogenetic mechanisms of lympho-hematopoietic disorders and for screening candidates of drugs for the disorders. BGIF genes may also be applied to gene therapy of the diseases. Thus, this invention enables novel diagnosis and treatment of lympho-hematopoietic disorders.

The present invention is demonstrated with reference to the following Examples, but is not to be construed as being limited thereto.

EXAMPLE 1

Identification of a New Downregulator of Lympho-hematopoiesis, BGIF 1.1 Cell Culturing A human renal cell carcinoma cell line 293T, a mouse stromal clone BMS2 (Pietrangeli, C. E. et al., 1988, Eur. J. Immunol. 18: 863–872) and its subclone, BMS2.4 (Kincade, K. W. et al., 1991, Adv. Exp. Med. Biol. 292: 227–234), and mouse myeloid leukemia cell lines WEHI3 (ATCC No. TIB-68) were maintained in Dulbecco's modified Eagle's medium (Nakalai Tesque, Kyoto, Japan) supplemented with 10% fetal calf serum (FCS; GIBCO, Grand Island, N.Y.).

1.2 Screening of a BMS2.4 cDNA Library

A subclone of a bone marrow derived stromal cell line, BMS2.4, produces soluble factors which inhibit proliferation of several types of hematopoietic cell lines (Kincade, K. W. et al., 1991, Adv. Exp. Med. Biol. 292: 227–234; Oritani, K. et al., 1999, Blood 93: 1346–1354). Neutralizing antibodies to TNF-α, TGF-β, or IFN-β did not block the effects of BMS2.4 supernatant. Thus, the growth inhibitory effects were not readily attributed to any of these factors. To identify the unique BMS2.4 products, we performed expression cloning on the basis of growth inhibition.

Polyadenylated RNA was isolated from BMS2.4 cells using a Fast Track mRNA isolation kit (Invitrogen, San Diego, Calif.). Double-stranded cDNA was synthesized with a TimeSaver cDNA systhesis kit (Pharmacia, Uppsala, Sweden), ligated with BstXI adaptors (Invitorogen), and cloned into a mammalian expression vector, pEF-BOS (S. Mizushima and S. Nagata, 1990, Nucl. Acids Res. 18: 5322). Plasmid cDNAs were purified from pools of a few hundreds of clones, and were transfected into 293T cells by calcium phosphate precipitation method. Supernatants from each transfectant were recovered and examined for growth inhibitory effects.

A myelomonocytic leukemia cell line, WEHI3, was particularly sensitive and was used as a target. Supernatants from the transfectants of 293T cells were added into cultures of WEHI3 cells, and the proliferation of the cells was evaluated by 3-(4,5-dimethylthiazol)-2,5-diphenyl tetrazolium bromide rapid colorimetric assay (MTT assay). The triplicate aliquots of cells were cultured in 96-well, flat bottom microtiter plates. MTT (10 μL of 5 mg/mL solution in PBS) was added for the final 4 hours of cultures, and then 100 μL of acid-isopropanol (0.04N HCl in isopropanol) was added and mixed. The optical density was measured on the Microelisa plate reader (Corona Electric, Ibaraki, Japan) with a test wavelength of 540 nm.

Figure 1:
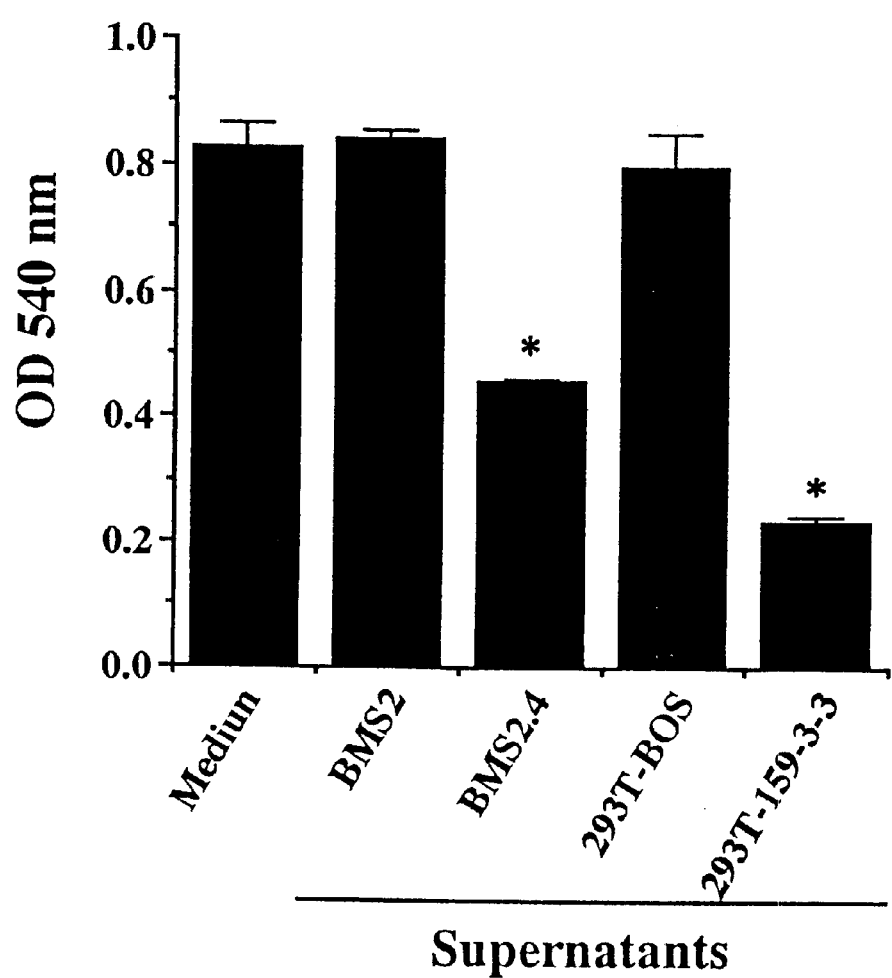
FIG. 1 illustrates that the clone 159-3-3 is carrying cDNA that encodes growth inhibitor of WEHI3. The cloned 159-3-3 plasmid or a control plasmid, pEF-BOS, were transfected into 293T cells with a calcium phosphate precipitation method, and supernatants from each transfectant were collected after 3 days cultures. BMS2 and BMS2.4 cells were cultured for 3 days after their confluent condition, and their supernatants were collected. WEHI3 cells ($5 \times 10^3$/well) were cultured in the presence of 10% of the indicated supernatants for two days. Their proliferation was evaluated by MTT assay. Statistically significant differences from control values are indicated an asterisk ($p<0.01$).

The library was screened based on inhibition of the growth of WEHI3 cells. A positive pool was divided into progressively smaller pools and rescreened until a single clone was isolated. We screened approximately 1×10$^5$ clones and isolated a single clone (clone 159-3-3) whose insert DNA encoded a growth-inhibitor of WEHI3 cells. As shown in FIG. 1, the supernatant of 293T cells transfected with the cloned 159-3-3 plasmid as well as BMS2.4-supernatant suppressed proliferation of WEHI3 cells.

EXAMPLE 2

Idetification of BGIF Protein 2.1 Primary Structure

The insert of the isolated clone was subcloned into pBluescript (Stratagene, La Jolla, Calif.), and nucleotide sequence was determined using an automated DNA sequencer (Applied Biosystems, Foster City, Calif.). The cloned plasmid 159-3-3 contains a 997 bp cDNA insert (FIG. 2, SEQ ID NO: 1). Nucleotide data base searching was performed with BLAST and FASTA from the GGG computer program (Genetics Computer Group, Madison, Wis.). No previously reported cDNAs or genomic DNAs are identical to this sequence, and we designated this cloned molecule as Blood Cell Growth-Inhibiting Factor, BGIF. The predicted protein translated from the first ATG is composed of 33 amino acids (SEQ ID NO: 2). In contrast, the predicted protein translated from the second ATG is composed of 182 amino acids (SEQ ID NO: 3), and has a highly hydrophobic stretch of 21 amino acid residues (SEQ ID NO: 4) at the N-terminal end that is appropriate for a signal peptide.

2.2 Identification of Functional Protein

We analyzed which ATG of BGIF cDNA is functional. First, we constructed the 1st-ATG/pRL-SV40 or the 2nd-ATG/pRL-SV40 plasmid to produce renilla luciferase translated from the first or the second ATG of BGIF under the control of the SV40 early enhancer/promoter, respectively.

For the construct to produce renilla luciferase using the first ATG of BGIF, BGIF cDNA was amplified by PCR with 5'-GGGCTGCAGTCAGCGAGCAAGAGCCCGAAG-3' (SEQ ID NO: 5), and 5'-GGGGCTAGCCACAGGCAGCATGCTGAAGCTTGA-3' (SEQ ID NO: 6). For the construct to produce renilla luciferase protein using the second ATG of BGIF, BGIF cDNA was amplified by PCR with 5'-GGGCTGCAGTCAGCGAGCAAGAGCCCGAAG-3' (SEQ ID NO: 5) and 5'-GGGGCTAGCACAGGCAGCATGCTGAAGCTTGA-3' (SEQ ID NO: 7). The amplified fragments were digested with PstI and NheI, and cloned into the pRL-SV40 plasmid (Promega, Madison, Wis.) whose original ATG site for the renilla luciferase protein had been destroyed by direct site mutagenesis (1st-ATG/pRL-SV40 and 2nd-ATG/pRL-SV40). The renilla luciferase protein was translated from the ATGs of BGIF cDNA in the 1st-ATG/pRL-SV40 and the 2nd-ATG/pRL-SV40 under the control of the SV40 early enhancer/promoter. All plasmid constructs were confirmed by sequencing.

These plasmids were transfected into BMS2.4 or BMS2 cells to perform luciferase assay. Luciferase assay was performed by using Dual-Luciferase Reporter System (Promega, Madison, Wis.), in which transfection efficiency was monitored by co-transfected pGL-Control Vector (Promega), an expression vector of firefly luciferase. The cultured cells were transfected with 10 μg of 1st-ATG/pRL-SV40 or the 2nd-ATG/pRL-SV40 together with 5 μg of pGL-Control Vector by lipofectamine transfection method. The transfected cells were lysed in lysis buffer supplied by the manufacturer, followed by measurement of the firefly and the renilla luciferase activities on luminometer LB96P (Berthold Japan, Tokyo, Japan). The relative renilla luciferase activities were calculated by normalizing transfection efficiency according to the fire fly luciferase activities.

Figure 3:
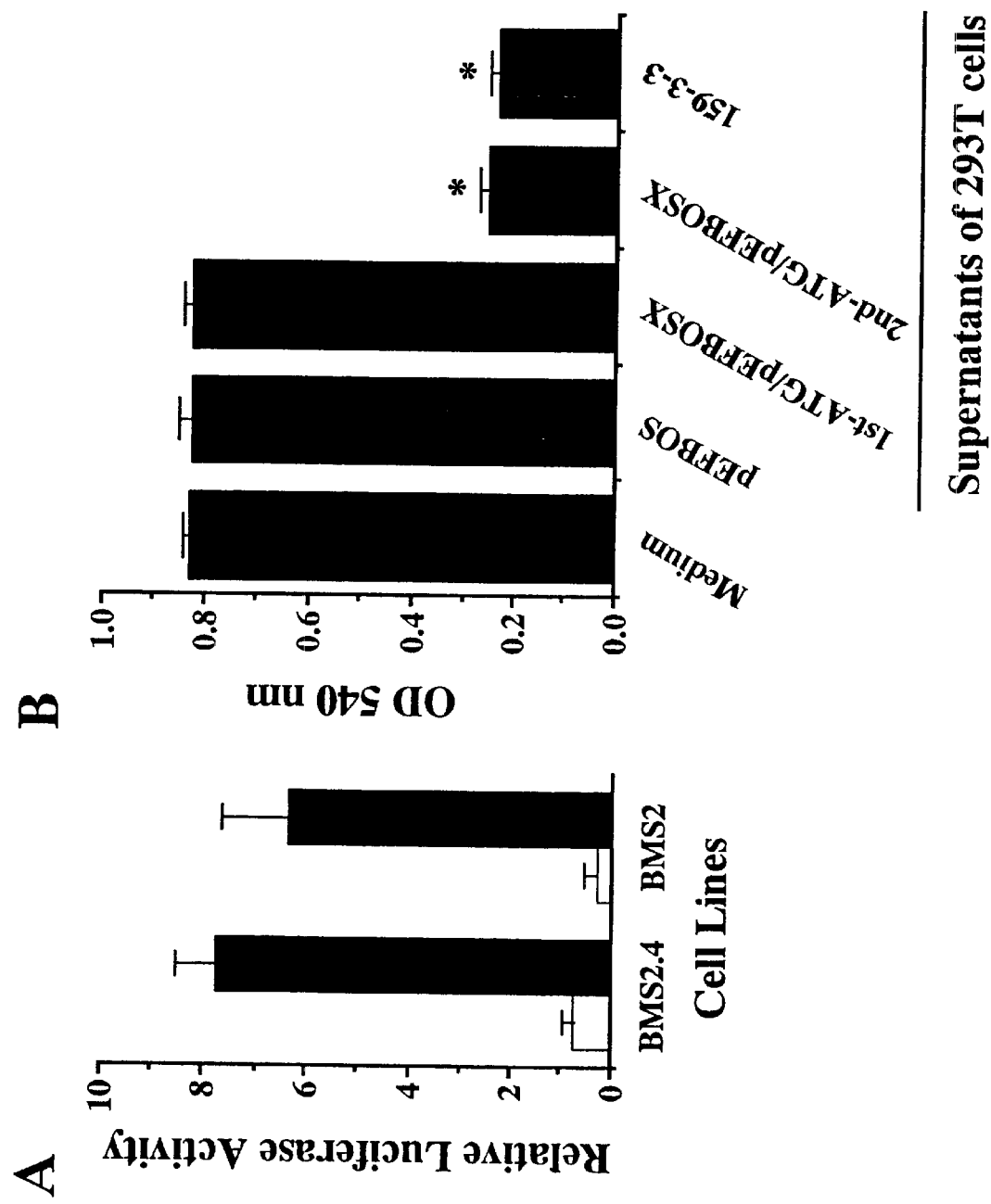
FIG. 3 illustrates that a product translated from the second ATG of BGIF is a major and functional protein. (A) shows relative renilla luciferase activities of BMS2.4 and BMS2 cells that were transfected with 1st-ATG/pRL-SV40 (open column) or the 2nd-ATG/pRL-SV40 (closed column), together with pGL-Control Vector by lipofectamine transfection. After 2 days cultures, cells were collected and subjected to luciferase assays. The relative renilla luciferase activities were calculated by normalizing transfection efficiency according to the firefly luciferase activities. Statistically significant differences from control values are indicated by an asterisk ($p<0.01$). (B) shows effects of culture supernatants of 293T cells that were transfected with plasmids, 1st-ATG/pEFBOSX and 2nd-ATG/pEFBOSX, with a calcium phosphate precipitation method. The transfectants were cultured for 3 days, and then their supernatants were collected. WEHI3 cells ($5 \times 10^3$/well) were cultured in the presence of 10% of the indicated supernatants for 2 days. Their proliferation was evaluated by MTT assay.

Renilla luciferase translated from the second ATG of BGIF was mainly produced (FIG. 3A).

Next, we produced proteins that were translated from the first or the second ATG.

To produce proteins that are translated from the first or the second ATGs of BGIF, BGIF cDNA was amplified by PCR. The oligonucleotide primers used for these reactions were as follows:
5'-GGGCTCGAGTCAGCGAGCAAGAGCCCGAAG-3' (SEQ ID NO: 8) and 5'-GGGCTCGAGCTGGGCTGCAGCTCAGCA-3' (SEQ ID NO: 9) for the protein that was translated from the first ATG; 5'-GGGCTCGAGAATCGTCAAGCTTCAGCA-3' (SEQ ID NO: 10) and 5'-GGGCTCGAGCTTCTCCTCATCTTGGGC-3' (SEQ ID NO: 11) for the protein that was translated from the second ATG. The amplified fragments were digested with XhoI, and cloned into a pEFBOSX plasmid that was yielded by site-directed mutagenesis to remove the XhoI site at 3524 of pEF-BOS (1st-ATG/pEFBOSX and 2nd-ATG/pEFBOSX). All plasmid constructs were confirmed by sequencing.

These plasmides were transfected into 293T cells. Each supernatant from the transfectants was recovered and added into cultures of WEHI3 cells to examine their growth. Supernatant of 293T cells transfected with 2nd-ATG/pEFBOSX, but not that of 293T cells trasnfected with 1st-ATG/pEFBOSX, inhibited proliferation of WEHI3 cells (FIG. 3B). Therefore, a functional product of BGIF is translated from the second ATG.

As shown in FIG. 2, the deduced BGIF protein has a highly hydrophobic stretch of 21 amino acid residues at the N-terminal end, but lacks an internal membrane spanning domain, suggesting that BGIF is a secreted protein. The protein sequence contains one Asn-X-Ser/Thr potential N-linked glycosylation sites at the position of amino acid 68, consistent with the hypothesis that BGIF may be glycosylated. As a result of computer search of BGIF sequence using FASTA and BLAST programs, BGIF has a similarity with IFN-α (31.9% identity in 166 amino acid overlap) and IFN-β (25.9% identity in 166 amino acid overlap) at the amino acid level (FIG. 4). However, six cystaine residues in the BGIF protein were not identical to those of IFN-α or IFN-β.

EXAMPLE 3

Gene Expression of BGIF in Hematopoietic Organs

Gene expression of BGIF was examined by Northern blot analysis. PolyA$^+$ RNAs were isolated using a Fast Track mRNA isolation kit (Invitrogen), electrophoresed through a formaldehyde agarose gel, and transferred onto a nylon membrane (Amersham). The cDNA fragments were labeled with $^{32}$P-dCTP using a random primed DNA labeling kit (Boehringer Mannheim, Indiapolis, Ind.) and hybridized to the membrane. Blots were then washed and autoradiographed.

Northern blot analysis revealed that the message size of BGIF was approximately 1 kb and that BMS2.4, but not WEHI3, expressed BGIF mRNA (FIG. 5A). In addition, RT-PCR was used to survey expression in mouse bone marrow and spleen. Total RNAs (2.5 µg) were reverse transcribed to cDNA in total reaction volume of 50 µL comprised of M-MLV reverse transcriptase (GIBCO), oligo dT (1 µg), 0.1 M DTT, 10 mM each dNTP, and 1×RT buffer. To perform PCR, 10 µL of the above RT mixtures were added to PCR buffer containing 1.5 mM MgCl$_2$, 1 U Taq polymerase (Perkin Elmer, Branchburg, N.J.), 2 mM each dNTP, and relevant sense and antisense primers. The oligonucleotide primers used for these reactions were as follows: 5'-TCCAGCGTCCAGCGCAGC-3' (SEQ ID NO: 12) and 5'-AGCACTTGCAGCTCACGC-3' (SEQ ID NO: 13) for BGIF; 5'-CCTAAGGCCAACCGTGAAAAG-3' (SEQ ID NO: 14) and 5'-TCTTCATGGTGCTAGGAGCCA-3' (SEQ ID NO: 15)-actin. PCR reaction mixtures were amplified under the following conditions: 28 cycles of 94 for 1 min, 55 for 2 min, 72 for 3 min.

As shown in FIG. 5B, 509 bp of PCR-amplified band was observed from the RT sample of BMS2.4 mRNA. Same size of products were observed, when RNAs of cultured bone marrow or spleen adherent cells as well as those of freshly isolated bone marrow spleen cells were subjected to RT-PCR. This amplification was specific to BGIF, because the PCR products were confirmed by sequencing.

Therefore, BGIF mRNA is expressed in bone marrow and spleen, at least by some of bone marrow and spleen stromal cells.

EXAMPLE 4

Effects of BGIF on Lympho-hematopoietic Cell Lines

To analyze functions of BGIF, an Ig/pEFBOSX vector (Oritani, K. and Kincade P. W., 1996, J. Cell. Biol. 134: 771–782) was used to produce Ig fusion proteins that were composed of CH2+CH3 cassette of human IgG1. The entire coding region of BGIF cDNA was amplified by PCR with 5'-GGGGCGGCCGCCGCAATCGTCAAGCTTCA-3' (SEQ ID NO: 16) and 5'-GGGCTCGAGCTTGGGCCTCTTCTCGCAGA-3' (SEQ ID NO: 17) and the PCR sample was digested with NotI and XhoI, and ligated into an Ig/pEFBOS vector (BGIF-Ig/BOS). Plasmid constructs were confirmed by sequencing.

The fusion protein prepared form BGIF and Ig (BGIF-Ig) was purified with protein A column (Pierce, Rockford, Ill.) from the supernatant of 293T cells transfected with the BGIF-If/BOS plasmid. CD44-Ig (Oritani, K. and Kincade P. W., 1996, J. Cell. Biol. 134: 771–782) that was composed of CD44 and the constant region of human IgG was prepared in the same way, and used as a negative control.

These purified proteins were added to cultures of WEHI3 cells to examine their effects on the growth of WEHI3 cells. BGIF-Ig, but not CD44-Ig, exhibited growth-inhibiting effects on WEHI3 cells in a dose dependent manner and its maximal activity was observed at the concentration of 10 ng/mL. CD44-Ig fusion protein had no growth-inhibiting effects.

A large panel of lympho-hematopoietic cell lines were cultured in the presence of 100 ng/mL of BGIF-Ig or CD44-Ig for 48 hours, and their proliferation and viability were evaluated (Table 1).

Mouse myeloid leukemia cell line, M1, was maintained in Dulbecco's modified Eagle's medium (Nakalai Tesque, Kyoto, Japan) supplemented with 10% fetal calf serum (FCS; GIBCO, Grand Island, N.Y.). Mouse pre-B cell clones, 1A9, BC7.12, BC7.7, 2E8, and F10 were maintained in McCoy's 5A medium (GIBCO) supplemented with 5% FCS and 5×10$^5$ M 2-mercaptoethanol in the presence of 1 ng/mL IL-7 (R&D Systems, Minneapolis, Minn.). Mouse lymphoma cell lines (7OZ/3, WEHI231, BW5147, BCL1, SP2/0,and EL4) and a virus transformed pre-B cell line, 18.81, were maintained in RPMI 1640 medium (Nakalai Tesque) supplemented with 10% FCS and 5×10$^5$ M 2-mercaptethanol. A mouse multipotent cell line, EML-C1, was maintained in Iscove's modified Dulbecco's medium (GIBCO) supplemented with 20% horse serum (ICN Biomedical Inc. Costa Mesa, Calif.) and 10 ng/mL SCF.

Cell growth was analyzed by $^3$H-thymidine incorporation assay. The triplicate aliquots of cells were cultured in 96-well, flat bottom microtiter plates. Each well was pulsed for 4 hours with 0.5 µCi $^3$H-thymidine (sp. act.: 5 Ci/mM; Amersham International, Amersham, Bucks, UK). The cells were then harvested with a semiauotmatic cell harvester (model 1295; Pharmacia LKB Biotechnology, Piscataway, N.J.), and the $^3$H-thymidine incorporation was measured with a liquid scintillation counter.

The effect of BGIF proteins is expressed as the stimulation index (S.I.) (thymidine uptake (cpm) in the presence of BGIF-Ig/thymidine uptake (cpm) in the presence of CD44-Ig). Viability of cells was assessed by the tripan blue exclusion assay. All values represent mean of two independent experiments.

TABLE 1

| Cell line | Histology | Proliferation (S.I.) | Loss of viability (%) |
|---|---|---|---|
| BC7.12 | Pre-B (LTBMC-derived) | 0.01** | 98.2** |
| 1A9 | Pre-B (LTBMC-derived) | 0.10** | 61.4** |
| 2E8 | Pre-B (LTBMC-derived) | 0.12** | 72.5** |
| F10 | Pre-B (LTBMC-derived) | 0.32** | 0.2 |
| BC7.7 | Pre-B (LTBMC-derived) | 0.59** | 1.2 |
| 18.81 | Pre-B (virus transformed) | 0.61** | −0.5 |
| 7OZ/3 | B lymphoma | 0.74** | −2.3 |
| WEHI231 | B lymphoma | 0.61** | −1.2 |
| BCL1 | B lymphoma | 0.98 | −0.9 |
| SP2/0 | Myeloma | 0.69** | 1.6 |
| EL4 | T lumphoma | 0.95 | 0.1 |
| BW5147 | T lumphoma | 0.63** | 1.3 |
| EML-C1 | Multipotent | 0.86* | 1.1 |
| WEHI3 | Myelomonocytic leukemia | 0.19** | 0.2 |
| WEHI279 | Myelomonocytic leukemia | 0.85* | 2.8 |
| M1 | Myelomonocytic leukemia | 1.01 | 0.0 |

Statiscally significant differences from control are indicated by one (p0.05) or two (p0.01) asterisks.

As shown in Table 1, BGIF-Ig suppressed the proliferation of B lineage cell lines (1A9, BC7.12, BC7.7, F10, 2E8, 18-81, 7OZ/3, WEHI231, SP2/0), a T lymphoma cell line (BW1597), myelomonocytic leukemia cell lines (WEHI3, WEHI279), and a multipotent cell line (EML-C1). In contrast, lymphoma cell lines (BCL1 and EL4) and a myeloid cell line (M1) were not affected by BGIF-Ig. While most of the cell lines did not die in response to this substance, three of five LTBMC-derived pre-B cell clones (1A9, BC7.12, 2E8) lost their viability. It is noteworthy that F10 cells derived from a BCL-2 transgenic mice were resistant to the cell death elicited by BGIF-Ig.

Counts of viable WEHI3 and BC7.12 cells treated with BGIF-Ig or CD44-Ig were performed every day (FIG. 6A). The doubling time of WEHI3 cells was prolonged from 12 h with the control CD44-Ig fusion protein to 24 h by exposure to BGIF-Ig.

DNA nuclear content in the cellular nucleus was also analyzed. After stimulation, cells ($1 \times 10^6$) were washed and resuspended in 100 μl of PBS, and then fixed by addition of 900 μl of cold ethanol. The fixed cells were incubated with 300 μl of staining buffer (1mg/ml RNase, 20 μg/ml propidium iodide, and 0.01% NP-40 in PBS) at 37 for 10 mim. DNA contents were then evaluated with FACSort (Becton Dickinson, Mountain View, Calif.) using Cell Quest software.

As shown in FIG. 6b, analysis of DNA nuclear content revealed that BGIF reduced S-phase population and increased G0/G1-phase population in WEHI3 cells (G0/G1-phase; 70.4% with BGIF-Ig, 50.1% with CD44-Ig, S-phase; 14.7% with BGIF-Ig, 35.1% with CD44-Ig). In contrast, BC7.12 cells lost their viability when treated with BGIF-Ig (FIG. 6A). The death of BC7.12 was due to apoptosis, because a subdiploid peak of DNA appeared within 24 h after the treatment with BGIF-Ig (FIG. 6B; 43.7% with BGIF-Ig, 0.3% with CD44-Ig).

DNA fragmentation in the cell nucleus was examined. DNA fragmentation was assayed as described in Oritani, K. et al., Blood 93, 1346–1354 (1999). After treatment with BGIF-Ig or CD44-Ig, cells ($1 \times 10^7$) were lysed in 0.4 ml lysis buffer containing 200 mM Tris-HCl, 100 mM EDTA, 1% SDS, and 50 μg/ml proteinase K, and incubated for 4 h at 37. DNAs were extracted with phenol, and then with chloroform/isoamylalcohol. An aqueous phase was collected and precipitated with NaCl and ethanol. DNA pellets were suspended in 0.4 ml TE buffer, and treated with 50 μg/ml RNase for 5 h and then with 200 μg/ml proteinase K for 5 h. DNAs were extracted twice and precipitated as above. DNA pellets were resuspended in TE buffer, separated by electrophoresis in 1% agarose gel (1 μg DNA per lane), and stained with 0.5 μg/ml ethidium bromide, and visualized under ultraviolet light.

DNAs obtained from BC7.12 cells cultured with BGIF-Ig for 24 h showed extensive degradation with oligonucleosomal fragments (FIG. 6C). Therefore, BGIF induced G0/G1-arrest or G1-prolongation in WEHI3 cells and apoptosis in BC7.12 cells.

EXAMPLE 5

Influence of BGIF on Normal Lympho-hematopoietic Cells

Colony assays were used to evaluate the influence of BGIF on normal lympho-hematopoiesis.

Bone marrow or spleen cells were prepared and suspended in 1 ml assay medium as described in Medina, K. L., Smithson, G. & Kincade, P. W., J. Exp. Med. 178, 1507–1515 (1995) and Yokota, T. et al., Blood 91, 3263–3272 (1998). The semisolid agar colony-forming unit assay for B lymphocyte precursors (CFU-IL-7) was performed with 1 ng recombinant mouse IL-7. Clonable B cells (CFU-B) were enumerated in semisolid agar containing 25 μg lipopolysaccharide. The progenitor assay for myeloid cells (CFU-GM) and erythroid cells (BFU-E) was performed in methylcellulose media (Veritas, Vancouver, Canada) consisting of IMDM, 0.9% methylcellulose, $10^{-4}$ M 2-mercaptoethanol, 2mM L-glutamine, 30% FCS, 1% deionized crystallized bovine serum albumin, 3 U/ml erythropoietin, 100 ng/ml stem cell factor, 3 ng/ml IL-3, and 10 ng/ml IL-6. All colony assays were performed in 35-mm dishes and incubated at 37 for 6 days.

As shown in FIG. 7, the cloning efficiency of mature mitogen responsive B cells (CFU-B: B lymphocyte colony-forming units) was only slightly decreased by addition of BGIF-Ig (43.3±2.49 with BGIF-Ig, 53.0±2.94 with CD44-Ig per $2.5 \times 10^4$ spleen cells). However, interleukin (IL)-7 responding pre-B cells (CFU-IL-7: IL-7 responding colony-forming units) were dramatically influenced and their clonal proliferation was decreased approximately 50% (66.0±4.90 with BGIF-Ig, 121.0±3.74 with CD44-Ig per $5 \times 10^4$ bone marrow cells). This inhibition was highly specific and BGIF had no influence on the responsiveness of myeloid progenitors to colony stimulating factors (CFU-GM: granulocyte-macrophage colony-forming units) or that of erythroid progenitors to erythropoietin (BFU-E: erythroid burst colony-forming units). We then used the OP42 stromal cell clone along with IL-7 to selectively support the production of B lineage lymphocytes in short term cultures. Addition of BGIF-Ig substantially reduced the yield of B lymphocytes in this model (data not shown). More complex LTBMC were then exploited to investigate the influence of BGIF on lympho-hematopoiesis.

LTBMC of lymphoid cells (W/W cultures) were initiated and maintained according to published methods (Whitlock, C. A., Robertson, D. & Witte, O. N., J. Immunol. Methods 6, 7353–7569 (1984)). Briefly, $6 \times 10^6$ bone marrow cells were cultured in 25-cm$^2$ flasks in 5% $CO_2$ at 37. The medium consisted of RPMI 1640 supplemented with $5 \times 10^{-5}$ M 2-mercaptoethanol and 5% FCS. LTBMC of myeloid cells (Dexter cultures) were initiated and maintained by methods originally described by Dexter et al. (Dexter, T. M. & Testa, N. G., Methods Cell Biol. 14, 387–405 (1976)). Briefly, $9 \times 10^6$ bone marrow cells were cultured in 25-cm$^2$ flasks in 5% $CO_2$ at 33. The culture medium consisted of α-MEM supplemented with $10^{-7}$ M hydrocortisone and 20% horse serum (HyClone, Logan, Utah). In both types of cultures, half the medium was replaced weekly with fresh medium.

Adherent layers of Whitlock-Witte (W/W) cultures typically contains macrophages, endothelial and fat cells, in addition to stromal cells, while the latter is thought to be sufficient to support lymphocyte formation from early progenitors (Whitlock, C. A., Robertson, D. & Witte, O. N., J. Immunol. Methods 6, 7353–7569 (1984)). Adherent layers formed normally in the presence of the control CD44-Ig fusion protein and the cultures produced foci of lymphoid cells (FIG. 8). In contrast, adherent cells were sparse in cultures containing BGIF-Ig and they did not support the formation of lymphoid cells. In Dexter cultures, BGIF-Ig did not affect either the formation of adherent layers or the production of myeloid cells. These findings open the possibility that BGIF may influence the lympho-hematopoietic microenvironment, in addition to its direct effect on lymphoid progenitors.

EXAMPLE 6

BGIF Utilizes the IFN-α/β Receptors and Induces IFN Regulatory Factor (IRF)-1

BGIF has weak homology with IFN-α, IFN-β, and IFN-ω. We analyzed whether BGIF displays its biological effects via the IFN-α/β receptors. A CFU-IL-7 colony assay was performed using IFN-α/β receptor knock out mice (IFN-α/βR$^{0/0}$) (Muller, U. et al., Science 264, 1918–1921 (1994)). In wild type 129Sv mice (WT), BGIF-Ig reduced CFU-IL-7 colony formation (FIG. 9A). However, BGIF-Ig did not inhibit the IL-7 dependent clonal expansion of lymphocyte precursors derived from mice whose IFN-α/β receptors were destroyed. IRF-1 is known to be a downstream effector of the IFN receptors and inducible by the IFN receptor ligation. As shown in FIG. 9B, BGIF-Ig induced expression of the IRF-1 gene, while IRF-2 was expressed constitutively and was not affected by BGIF-Ig. These findings indicate that BGIF influences B lymphocyte precursors via the IFN-α/β receptors and induces at least one mediator of IFN action.

EXAMPLE 7

Signal Transduction Pathway Utilized by BGIF

Cytokine functions are mainly mediated by the Janus kinase (Jak) family of protein tyrosine kinases along with signal transducers and activators of transcription (Stat) (Ihle, J. N., Cell 84, 331–334 (1996)). Tyrosine phosphorylation of Jak-Stat proteins were analyzed after WEHI3 and BC7.12 cells were exposed to BGIF-Ig or CD44-Ig respectively.

Immunoprecipitation, gel electrophoresis, and immunoblotting were performed according to methods described previously (Matsumura, I. et al., Mol. Cell. Biol. 17, 2933–2943 (1997)). Briefly, cells were serum-starved, stimulated with BGIF-Ig, and then lysed in lysis buffer. After insoluble material was removed by centrifugation, the lysates obtained from $1 \times 10^7$ cells were incubated with 1 μg of the indicated antibodies, followed by the addition of protein G sepharose beads (Amersham). The immunoprecipitates were subjected to sodium dodecyl sulfate-polyacrylamide gel electrophoresis. The proteins were electrophoretically transferred onto a polyvinylidene difluoride membrane (Immobilion; Millipore Corp., Bedford, Mass.). After blocking of residual binding sites on the filter, immunoblotting was performed with the appropriate antibodies. Immunoreactive proteins were visualized with the enhanced chemiluminescence detection system (DuPont NEN, Boston, Mass.).

In WEHI3 cells, BGIF-Ig induced tyrosine phosphorylation of Jak1, Jak2, Tyk2, Stat1, and Stat3, but not that of Jak3 (FIG. 10A). Stat5 molecule was constitutively phosphorylated and was not affected by BGIF-Ig. Activation of Stat1 and Stat3 was also indicated by the fact that treatment WEHI3 cells with BGIF-Ig induced expression of the Stat1-dependent gene, IRF-1 (FIG. 9B). Jun-B is a Stat3-dependent gene and it was also induced (data not shown). In BC7.12 cells, BGIF-Ig induced tyrosine phosphorylation of Jak1, Tyk2, Stat1, and Stat5, but not that of Jak2, Jak3, or Stat3 (FIG. 10B). CD44-Ig did not induce tyrosine phosphorylation of any examined Jak-Stat proteins in both of cell lines. Therefore, BGIF activates Jak1, Tyk2, and Stat1 in several cell types, as well Jak2, Stat3, and Stat5 in certain cellular environments.

What is claimed is:

1. An isolated polypeptide selected from the group consisting of:
   (a) a polypeptide comprising the amino acid sequence as set forth in SEQ ID NO:3;
   (b) a polypeptide comprising a derivative of the amino acid sequence set forth in SEQ ID NO:3, in which one or more amino acids are substituted, deleted, inserted, and/or added, wherein said derivative amino acid sequence has a 80% or more sequence identity with the amino acid sequence set forth in SEQ ID NO:3; and
   (c) a polypeptide endoded by a DNA hybridizing with the DNA comprising the nucleotide sequence as set forth in SEQ ID NO:1, wherein hybridization is done at 42° C. overnight in a hybridization solution containing 25% formamide, 4×SSC, 50 mM Hepes pH 7.0 and 10×Denhardt's solution and 20 µg/ml denatured salmon sperm DNA and a labeled probe, followed by successive washings at room temperature with 2×SSC and 0.1% SDS,
   wherein said polypeptide suppresses the proliferation of lympho-hematopoietic cells.

2. The protein according to claim 1, wherein the lympho-hematopoietic cells are B lineage cell lines.

3. A peptide fragment of the polypeptide according to claim 1, wherein said peptide fragment suppresses the proliferation of lympho-hematopoietic cells.

4. A pharmaceutical composition comprising the polypeptide according to claim 1 as an active ingredient.

5. The pharmaceutical composition according to claim 4, wherein the composition is for treating lympho-hematopoietic disorders.

6. The polypeptide according to claim 1, wherein the polypeptide is a derivative which has an amino acid sequence having 90% or more sequence identity with the amino acid sequence set forth in SEQ ID NO:3.

7. A pharmaceutical composition, comprising:
   a pharmaceutically acceptable carrier; and
   a polypeptide comprising the amino acid sequence as set forth in SEQ ID NO:3.

8. A pharmaceutical composition, comprising:
   a pharmaceutically acceptable carrier; and
   a polypeptide comprising a derivative of the amino acid sequence set forth in SEQ ID NO:3 wherein the derivative has 90% or more sequence identity with the SEQ ID NO:3,
   wherein said polypeptide suppresses the proliferation of lympho-hematopoietic cells.

9. A pharmaceutical composition, comprising:

a pharmaceutically acceptable carrier; and a polypeptide encoded by a DNA hybridizing with the DNA comprising the nucleotide sequence as set forth in SEQ ID NO:1 wherein hybridizing is done at 42° C. overnight in a hybridization solution containing 25% formamide, 4×SSC, 50 mM Hepes pH 7.0 and 10×Denhardt's solution and 20 µg/ml denatured salmon sperm DNA and a labeled probe, followed by successive washings at room temperature with 2×SSC and 0.1% SDS, wherein said polypeptide suppresses the proliferation of lympho-hematopoietic cells.

* * * * *

UNITED STATES PATENT AND TRADEMARK OFFICE
CERTIFICATE OF CORRECTION

PATENT NO. : 6,518,043 B1
DATED : February 11, 2003
INVENTOR(S) : Oritani Kenji et al.

It is certified that error appears in the above-identified patent and that said Letters Patent is hereby corrected as shown below:

Column 1,
Line 6, please add the following header and paragraph:

GOVERNMENT RIGHTS
This invention was made with Government support under Grant No. AI33085, awarded by the National Institutes of Health. The government may have certain rights in this invention.

Line 21, please change as follows "system" to -- systems --
Line 31, please change as follows "cause" to -- causes --

Column 4,
Line 27, please change as follows "cultures" to -- of culture --

Column 8,
Line 45, please change as follows "42" to -- 42 degrees --

Column 11,
Line 66, please delete as follows "West"

Column 13,
Line 42, please change as follows "interfere" to -- interferes --

Column 19,
Line 11, please change as follows "37" to -- 37 degrees --

UNITED STATES PATENT AND TRADEMARK OFFICE
CERTIFICATE OF CORRECTION

PATENT NO. : 6,518,043 B1
DATED : February 11, 2003
INVENTOR(S) : Oritani Kenji et al.

It is certified that error appears in the above-identified patent and that said Letters Patent is hereby corrected as shown below:

Column 20,
Line 3, please change as follows "37" to -- 37 degrees --

Signed and Sealed this

Twenty-ninth Day of July, 2003

JAMES E. ROGAN
*Director of the United States Patent and Trademark Office*

SEQUENCE LISTING

```
<160> NUMBER OF SEQ ID NOS:   17

<210> SEQ ID NO 1
<211> LENGTH: 997
<212> TYPE: DNA
<213> ORGANISM: Mus musculus
<220> FEATURE:
<221> NAME/KEY: CDS
<222> LOCATION: (161)..(706)

<400> SEQUENCE: 1
agaagtcgcg tccagcgtcc agcgcagcgc aggcagtcag cgagcaagag cccgaagctc        60
cgagtgaact attaaagcag caaactccag gctcaatggg aaggcggcct tgccctcgcg       120 ctcccctgc aggccagccc cgcaatcgtc aagcttcagc atg ctg cct gtg cat        175
                                              Met Leu Pro Val His
                                               1               5 cta ttc ctg gtg gga ggg gtg atg ctg agc tgc agc cca gcc agc tca        223
Leu Phe Leu Val Gly Gly Val Met Leu Ser Cys Ser Pro Ala Ser Ser
           10                  15                  20 ctt gat tct ggt aaa tct ggg agc ctg cac ctg gag cgc agc gaa acc        271
Leu Asp Ser Gly Lys Ser Gly Ser Leu His Leu Glu Arg Ser Glu Thr
        25                  30                  35 gcg cgc ttc cta gca gag ctc cga agc gtg ccg ggt cac cag tgc ctg        319
Ala Arg Phe Leu Ala Glu Leu Arg Ser Val Pro Gly His Gln Cys Leu
    40                  45                  50 cgg gac agg acc gat ttc cca tgt ccc tgg aag gaa gga act aac atc        367
Arg Asp Arg Thr Asp Phe Pro Cys Pro Trp Lys Glu Gly Thr Asn Ile
55                  60                  65 aca cag atg act ctg gga gaa acc acc agt tgc tac tcc cag acc ctc        415
Thr Gln Met Thr Leu Gly Glu Thr Thr Ser Cys Tyr Ser Gln Thr Leu
70                  75                  80                  85
```

```
agg cag gtc ctc cac ctc ttt gac aca gag gcc agc aga gct gcc tgg      463
Arg Gln Val Leu His Leu Phe Asp Thr Glu Ala Ser Arg Ala Ala Trp
            90                  95                 100 cac gag agg gcg ctg gac cag cta cta tct agc ctg tgg cgt gag ctg      511
His Glu Arg Ala Leu Asp Gln Leu Leu Ser Ser Leu Trp Arg Glu Leu
            105                 110                 115 caa gtg ctg aag agc cca aga gag cag ggc cag tcc tgt cca ctg cct      559
Gln Val Leu Lys Ser Pro Arg Glu Gln Gly Gln Ser Cys Pro Leu Pro
            120                 125                 130 ttt gcc ctg gcc atc cgc acc tac ttc cga ggg ttc ttc cgc tat ctg      607
Phe Ala Leu Ala Ile Arg Thr Tyr Phe Arg Gly Phe Phe Arg Tyr Leu
135                 140                 145 aag gca aag gca cac agc gct tgc tcc tgg gag atc gtc aga gtc caa      655
Lys Ala Lys Ala His Ser Ala Cys Ser Trp Glu Ile Val Arg Val Gln
150                 155                 160                 165 ttg caa gtg gac ctt cca gcg ttc cca ctg tct gcg aga aga ggc cca      703
Leu Gln Val Asp Leu Pro Ala Phe Pro Leu Ser Ala Arg Arg Gly Pro
            170                 175                 180 aga tgaggagaag ccccgtgcag gaatctctct gctctcgtga caccacgctc           756
Arg cctctctcca ttcaaagcag acgcacggat tcggattcag caccaacagg cgaaatgggc    816
atgcatcgac caagaacatc gagttcttta tgtcttccct gccagaggcc ccgaagcatc    876
ctactgtaca tcatacactg cgaaagatgt tgaaagaaa acctgtgctc ttgcatttga     936
ggtggcttct gaataaattg atgatctcgg ttaaaaaaaa aaaaaaaaaa aaaaaaaaa     996 a                                                                    997
```

<210> SEQ ID NO 2
<211> LENGTH: 33
<212> TYPE: PRT
<213> ORGANISM: Mus musculus

<400> SEQUENCE: 2

```
Met Gly Arg Arg Pro Cys Pro Arg Ala Pro Pro Ala Gly Gln Pro Arg
 1               5                  10                  15

Asn Arg Gln Ala Ser Ala Cys Cys Leu Cys Ile Tyr Ser Trp Trp Glu
            20                  25                  30

Gly
```

<210> SEQ ID NO 3
<211> LENGTH: 182
<212> TYPE: PRT
<213> ORGANISM: Mus musculus

<400> SEQUENCE: 3

```
Met Leu Pro Val His Leu Phe Leu Val Gly Val Met Leu Ser Cys
 1               5                  10                  15

Ser Pro Ala Ser Ser Leu Asp Ser Gly Lys Ser Gly Ser Leu His Leu
            20                  25                  30

Glu Arg Ser Glu Thr Ala Arg Phe Leu Ala Glu Leu Arg Ser Val Pro
        35                  40                  45

Gly His Gln Cys Leu Arg Asp Arg Thr Asp Phe Pro Cys Pro Trp Lys
    50                  55                  60

Glu Gly Thr Asn Ile Thr Gln Met Thr Leu Gly Glu Thr Thr Ser Cys
65                  70                  75                  80

Tyr Ser Gln Thr Leu Arg Gln Val Leu His Leu Phe Asp Thr Glu Ala
            85                  90                  95
```

```
Ser Arg Ala Ala Trp His Glu Arg Ala Leu Asp Gln Leu Leu Ser Ser
            100                 105                 110

Leu Trp Arg Glu Leu Gln Val Leu Lys Ser Pro Arg Glu Gln Gly Gln
        115                 120                 125

Ser Cys Pro Leu Pro Phe Ala Leu Ala Ile Arg Thr Tyr Phe Arg Gly
    130                 135                 140

Phe Phe Arg Tyr Leu Lys Ala Lys Ala His Ser Ala Cys Ser Trp Glu
145                 150                 155                 160

Ile Val Arg Val Gln Leu Gln Val Asp Leu Pro Ala Phe Pro Leu Ser
                165                 170                 175

Ala Arg Arg Gly Pro Arg
            180

<210> SEQ ID NO 4
<211> LENGTH: 21
<212> TYPE: PRT
<213> ORGANISM: Mus musculus

<400> SEQUENCE: 4

Met Leu Pro Val His Leu Phe Leu Val Gly Val Met Leu Ser Cys
  1               5                  10                  15

Ser Pro Ala Ser Ser
            20

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5
gggctgcagt cagcgagcaa gagcccgaag                                    30

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
ggggctagcc acaggcagca tgctgaagct tga                                33

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
ggggctagca caggcagcat gctgaagctt ga                                 32

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:Artificially
```

Synthesized Primer Sequence

<400> SEQUENCE: 8
gggctcgagt cagcgagcaa gagcccgaag                                              30

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
gggctcgagc tgggctgcag ctcagca                                                 27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
gggctcgaga atcgtcaagc ttcagca                                                 27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
gggctcgagc ttctcctcat cttgggc                                                 27

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
tccagcgtcc agcgcagc                                                           18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
agcacttgca gctcacgc                                                           18

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

```
<400> SEQUENCE: 14
cctaaggcca accgtgaaaa g                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 15
tcttcatggt gctaggagcc a                                              21

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 16
ggggcggccg ccgcaatcgt caagcttca                                      29

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 17
gggctcgagc ttgggcctct tctcgcaga                                      29
```